(12) United States Patent
McCarthy et al.

(10) Patent No.: US 9,708,275 B2
(45) Date of Patent: Jul. 18, 2017

(54) HETEROCYCLIC COMPOUNDS AND METHODS FOR THEIR USE

(71) Applicant: Novartis AG, Basel (CH)

(72) Inventors: Thomas David McCarthy, Old Greenwich, CT (US); Alan Naylor, Royston (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/149,641

(22) Filed: May 9, 2016

(65) Prior Publication Data

US 2016/0257656 A1 Sep. 8, 2016

Related U.S. Application Data

(63) Continuation of application No. 14/373,355, filed as application No. PCT/AU2013/000061 on Jan. 25, 2013, now abandoned.

(30) Foreign Application Priority Data

Jan. 25, 2012 (AU) .............................. 2012900286

(51) Int. Cl.
   *C07D 241/04* (2006.01)
   *C07D 403/04* (2006.01)
   *A61K 31/495* (2006.01)
   *A61K 31/496* (2006.01)
   *C07D 413/04* (2006.01)
   *C07D 413/06* (2006.01)
   *C07D 243/08* (2006.01)
   *C07D 231/12* (2006.01)
   *C07D 295/185* (2006.01)

(52) U.S. Cl.
   CPC ......... *C07D 241/04* (2013.01); *C07D 231/12* (2013.01); *C07D 243/08* (2013.01); *C07D 295/185* (2013.01); *C07D 403/04* (2013.01); *C07D 413/04* (2013.01); *C07D 413/06* (2013.01)

(58) Field of Classification Search
   None
   See application file for complete search history.

(56) References Cited

U.S. PATENT DOCUMENTS

| 5,116,842 A | 5/1992 | Naylor et al. |
| 5,292,726 A | 3/1994 | Ashton |
| 5,344,830 A | 9/1994 | Mills et al. |
| 6,951,862 B2 | 10/2005 | Snutch |
| 2014/0378430 A1 | 12/2014 | McCarthy et al. |
| 2015/0218180 A1 | 8/2015 | McCarthy et al. |

FOREIGN PATENT DOCUMENTS

| WO | 94/13646 | 6/1994 |
| WO | 95/00498 | 1/1995 |
| WO | 2005/056015 | 6/2005 |
| WO | 2006/066361 | 6/2006 |

OTHER PUBLICATIONS

Office Action dated Aug. 3, 2015, corresponding Chinese Application No. 201380016259.9 based on PCT/AU2013/000061.
M.T. Wu et al, "Synthesis and Structure-Activity Relationships of a Novel Series of Non-Peptide AT2-Selective Angiotensin II Receptor Antagonists," Biorganic and Med. Chem. Letters, 3(10):2023-2028 (1993).
Extended European Search Report, May 11, 2015, corresponding European Application No. 13741446.2 based on PCT/AU2013/000061.
Chakrabarty, Endocrinology, 2008, 149(7); 3452-3460.
Clere, Int'l J. Cancer, 2010, 127: 2279-2291.
Izu, J. Biol. Chem., 2009, 248(4): 4857-4864.
Steckelings, Peptides, 2005, 26: 1401-1409.
Wallinder, Biorg & Med. Chem., 2008, 16: 6841-6849.
Wan, J. Med. Chem., 2004, 47: 5995-6008.
Wexler, J. Med. Chem., 1996, 39(3): 625-656.
Berellini, J. Med. Chem., 2005, 48(13): 4389-4399.
Jain & Yadav, Chem. Biol. Drug Des., 2008, 71: 271-277.
International Search Report for related application PCT/AU2013/000061, filed on Jan. 25, 2013 and mailed on Mar. 18, 2013.
PubChem Compound Summary for: CI D 44783574, Create Date: Mar. 15, 2010, 10 pages, retrieved on Jan. 31, 2016 from the Internet at https://pubchem.ncbi.nlm.nih.gov/compound/44783574.
Ballatore et al. ChemMedChem. Mar. 2013; 8(3): 385-395.
CA Registry Nos. 1350993-82-6 and 1350993-50-8, entered into the CA Registry File on Dec. 16, 2011, suppled by ChemBridge Corporation.
ChemBridge Product Guide, 2 pages, retrieved from the Internet at http://www.chembridge.com/screening_libraries/ on Aug. 9, 2015.

*Primary Examiner* — Emily Bernhardt
(74) *Attorney, Agent, or Firm* — Sophie Binet Cross

(57) ABSTRACT

The present invention relates to heterocyclic compounds useful for antagonizing angiotensin II Type 2 ($AT_2$) receptor. More particularly the invention relates to piperazine and diazepine compounds, compositions containing them and their use in methods of treating or preventing disorders or diseases associated with $AT_2$ receptor function including neuropathic pain, inflammatory pain, conditions associated with neuronal hypersensitivity, impaired nerve conduction velocity, cell proliferation disorders, disorders associated with an imbalance between bone resorption and bone formation and disorders associated with aberrant nerve regeneration.

6 Claims, No Drawings

HETEROCYCLIC COMPOUNDS AND METHODS FOR THEIR USE

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although the $AT_2$ receptor has been known since the 1980s, much less is known about its biological function than the angiotensin II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain, particularly inflammatory pain [WO 2007/106938] and neuropathic pain [WO 2006/066361], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohtuneral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells. Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

The present invention is predicated in part on the discovery of heterocyclic azetidine and pyrrolidine compounds that have $AT_2$ receptor antagonist activity.

SUMMARY OF THE INVENTION

In a first aspect of the present invention there is provided a compound of formula (I):

wherein
X is —$CHR^4$—, —$CH_2CHR^4$— or —C(=O)—;
$R^1$ is —C(=O)$CHR^5R^6$, —C(=O)$NR^5R^6$, —C(=O)$CH_2CHR^5R^6$, —C(=O)CH=$CR^5R^6$, —C(=S)$CHR^5R^6$, —C(=S)$NR^5R^6$, —C(=S)$CH_2CHR^5R^6$, —C(=S)CH=$CR^5R^6$, —C(=$NR^7$)$CHR^5R^6$, —C(=$NR^7$)$NR^5R^6$, —C(=$NR^7$)$CH_2CHR^5R^6$ or —C(=$NR^7$)CH=$CR^5R^6$;
$R^2$ is —$C_{1-6}$alkyl, —$C_{2-6}$alkynyl, —C(=O)$R^8$, —C(=O)$NHR^7$, —$SO_2N(R^7)_2$, —W— cycloalkyl, —W-cycloalkenyl, —W-aryl, —W-heterocyclyl, —W-heteroaryl, —W—Z—Y-cycloalkyl, —W—Z—Y-cycloalkenyl, —W—Z—Y-aryl, —W—Z—Y-heterocyclyl or —W—Z—Y-heteroaryl;
$R^3$ is a carboxylic acid, —$CH_2CO_2H$, —C(=O)C(=O)OH, —$CH_2OH$, —C(=O)$NH_2$, —$CH_2C$(=O)$NH_2$, —CN, —$CH_2CN$, a carboxylic acid biostere or a $CH_2$-carboxylic acid bioisotere;
$R^4$ is hydrogen or together with $R^2$ forms a fused cycloalkyl, cycloalkenyl, aryl, heterocyclyl or heteroaryl ring optionally substituted with one or two substituents selected from —$C_{1-6}$alkyl, —$C_{2-6}$alkenyl, —$C_{2-6}$alkynyl, cycloalkyl, cycloalkenyl, aryl, heterocyclyl, heteroaryl, —$C_{1-6}$alkylene$R^9$, —$C_{2-6}$alkenylene$R^9$, —$C_{2-6}$alkynylene$R^9$, —$OC_{0-6}$alkylene$R^9$, —$OC_{2-6}$alkenylene$R^9$, —$OC_{2-6}$alkynylene$R^9$, —C(=O)$C_{0-6}$alkylene$R^9$, —C(=O)$C_{2-6}$alkenylene$R^9$, —C(=O)$C_{2-6}$alkynylene$R^9$, —C(=O)$OC_{0-6}$alkylene$R^9$, —C(=O)$C_{2-6}$alkenylene$R^9$, —C(=O)$OC_{2-6}$alkynylene$R^9$, —$SO_2NHC_{0-4}$alkylene$R^9$, —$SO_2NHC_{2-6}$alkenylene$R^9$, —$SO_2NHC_{2-6}$alkynylene$R^9$, —$NHSO_2C_{0-6}$alkylene$R^9$, —$NHSO_2C_{2-6}$alkenylene$R^9$, —$NHSO_2C_{2-6}$alkynylene$R^9$, —NH(=O)$NHR^{10}$, —NHC(=O)$OR^{10}$ or —CH(OH)CH(OH)$R^{10}$;
$R^5$ and $R^6$ are independently selected from hydrogen, —$C_{1-6}$alkyl, —$C_{2-6}$alkenyl, —$C_{2-6}$alkynyl, cycloalkyl, cycloalkenyl, aryl, heterocyclyl, heteroaryl, —$CH_2$cycloalkyl, —$CH_2$cycloalkenyl, —$CH_2$aryl, —$CH_2$heterocyclyl and —$CH_2$heteroaryl; provided that both $R^5$ and $R^6$ are not hydrogen;

$R^7$ is hydrogen, —$C_{1-6}$alkyl, aryl or —$C_{1-6}$alkylenearyl;
$R^8$ is —$C_{1-6}$alkyl, —$C_{2-6}$alkenyl, —$C_{2-6}$alkynyl, aryl or —$C_{1-6}$alkylenearyl;
$R^9$ is cycloalkyl, cycloalkenyl, aryl, heterocyclyl, heteroaryl;
$R^{10}$ is —$C_{2-6}$alkenyl, —$C_{2-6}$alkynyl, cycloalkyl, cycloalkenyl, aryl, heterocyclyl or heteroaryl;
W is a covalent bond, —SO—, —$SO_2$— —C(=O)N($R^7$)—, —$C_{1-4}$alkylene-, —$C_{2-4}$alkenylene-, —$C_{2-4}$alkynylene-, —$C_{1-3}$alkyleneQ$C_{1-3}$alkylene-, —$C_{1-4}$alkyleneQ-, —$C_{2-4}$alkenyleneQ- or —$C_{2-4}$alkynyleneQ-;
Z is -cycloalkyl-, -cycloalkenyl-, -aryl-, -heterocyclyl- or -heteroaryl-;
Y is a covalent bond, —O—, —S—, —SO—, —$SO_2$— —N($R^7$)—, —N($R^7$)C(=O)—, —C(=O)N($R^7$)—, —$C_{1-3}$alkylene-, —$C_{2-3}$alkenylene-, —$C_{2-3}$alkynylene-, —$C_{1-3}$alkyleneQ$C_{1-3}$alkylene-, -Q$C_{1-4}$-alkylene-, -Q$C_{2-4}$ alkenylene-, -Q$C_{2-4}$alkynylene-, —$C_{2-4}$alkenyleneQ-, —$C_{2-4}$alkynyleneQ-, -Q$C_{1-4}$alkyleneQ-, -Q$C_{2-4}$alkenyleneQ- or -Q$C_{2-4}$alkynyleneQ-; and
Q is —O—, —S—, —SO—, —$SO_2$— —N($R^7$)—, —N($R^7$)C(=O)— or —C(=O)N($R^7$)—;
wherein each cycloalkyl, cycloalkenyl, aryl, heterocyclyl and heteroaryl is optionally substituted;
or a pharmaceutically acceptable salt thereof.

In another aspect, the present invention provides a pharmaceutical composition comprising the compounds of formula (I) or a pharmaceutically acceptable salt thereof and a pharmaceutically acceptable carrier.

In a further aspect of the invention, there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention, there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "$AT_2$ receptor" means an angiotensin II type 2 ($AT_2$) receptor polypeptide that can bind angiotensin II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The term "antagonist" as used herein refers to a compound that decreases or inhibits the biological activity and/or function of an $AT_2$ receptor, including binding to the $AT_2$ receptor and blocking access to angiotensin II, inhibiting a gene that expresses $AT_2$ receptor, or inhibiting an expression product of that gene. By the term "selective", is meant that the compound binds to and/or inhibits $AT_2$ receptor activity to a greater extent than binding and inhibition of the $AT_1$ receptor. In some instances, selective refers to binding and/or inhibition of the $AT_2$ receptor with little or no binding at the $AT_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally painful. A hyperalgesia condition is one that is associated with pain caused by a stimulus that is not normally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling, asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "alkylene" refers to a divalent saturated hydrocarbon chain having 1 to 6 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

As used herein, the term "alkenylene" refers to a divalent unsaturated hydrocarbon chain having 2 to 6 Carbon atoms and at least one double bond. Where appropriate, the alkenylene group may have a specified number of carbon atoms, for example, $C_{2-6}$alkenylene includes alkenylene groups having 2, 3, 4, 5 or 6 carbon atoms in a linear arrangement. The double bonds may be in either E or Z configuration. Examples of suitable alkenylene groups include, but are not limited to, —CH═CH—, —CH═CHCH$_2$—, —CH$_2$CH═CH—, —CH═CHCH$_2$CH$_2$—, —CH$_2$CH═CHCH$_2$—, —CH$_2$CH$_2$CH═CH—, —CH═CHCH$_2$CH$_2$CH$_2$—, —CH$_2$CH═CHCH$_2$CH$_2$—, —CH$_2$CH$_2$CH═CHCH$_2$—, —CH$_2$CH$_2$CH$_2$CH═CH—, —CH═CHCH$_2$CH$_2$CH$_2$CH$_2$— —CH$_2$CH═CHCH$_2$CH$_2$CH$_2$—, —CH$_2$CH$_2$CH═CH$_2$CH$_2$—, —CH$_2$CH$_2$CH$_2$CH═CHCH$_2$— and —CH$_2$CH$_2$CH$_2$CH$_2$CH═CH—.

As used herein, the term. "alkynylene" refers to a divalent unsaturated hydrocarbon chain having 2 to 6 carbon atoms and at least one triple bond. Where appropriate, the alkynylene group may have a specified number of carbon atoms, for example, $C_{2-6}$alkynylene includes alkynylene groups having 2, 3, 4, 5 or 6 carbon atoms in a linear arrangement. Examples of suitable alkynylene groups include, but are not limited to, —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, —C≡CCH$_2$CH$_2$CH$_2$—, —CH$_2$C≡CCH$_2$CH$_2$—, —CH$_2$CH$_2$C≡CCH$_2$—, —CH$_2$CH$_2$CH$_2$C≡C—, —C≡CCH$_2$CH$_2$CH$_2$CH$_2$— —CH$_2$C≡CCH$_2$CH$_2$CH$_2$—, —CH$_2$CH$_2$C≡CCH$_2$CH$_2$—, —CH$_2$CH$_2$CH$_2$C≡CCH$_2$— and —CH$_2$CH$_2$CH$_2$CH$_2$C≡C—.

In some embodiments, one or more "—CH$_2$—" groups in an alkylene, alkenylene or alkynylene group may be replaced by a heteroatom or a group containing a heteroatom including —O—, —S—, —NH—, —NR—, —S(O)—, —S(O)$_2$—, —C(O)—, —C(═O)NH— and —NHC(═O)—.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl and tetrazolyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, oxo (═O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —CO$_2$H, —CO$_2$C$_{1-6}$alkyl, —NH$_2$, —NH(C$_{1-6}$alkyl), —N(C$_{1-6}$alkyl)$_2$, —NH(phenyl), —N(phenyl)$_2$, oxo, —CN, —NO$_2$, -halogen, —CF$_3$, —OCF$_3$, —SCF$_3$, —CHF$_2$, —OCHF$_2$, —SCHF$_2$, -phenyl, -heterocyclyl, -heteroaryl, -heteroaryl, —Oheterocyclyl, —Ophenyl, —C(═O)phenyl, —C(═O)C$_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —CO$_2$H, —CO$_2$CH$_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The term "carboxylic acid bioisotere" refers to a group which is physiochemically; or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—PO$_3$H$_2$), —C(OH)(CF$_3$)$_2$, N-(aryl or heteroaryl)-sulfonamides, acylsulfonamides and sulfonic acid (—SO$_3$H) [See Patani and LaVoie, 1996]. Examples of sulfonamide isosteric equivalents of carboxy groups include —C(=O)NHSO$_2$R$^a$, —C(=O)NHSO$_2$N(R$^a$)$_2$, —C(=O)NHSO$_2$NH(R$^a$), —SO$_2$NHC(=O)R$^a$, —SO$_2$NHC(=O)NHR$^a$, —SO$_2$NHR$^a$ and —NHSO$_2$R$_a$, where R$^a$ is selected from the group consisting of C$_{1-6}$alkyl, C$_{2-6}$alkenyl, C$_{3-8}$cycloalkyl, aryl, heterocyclyl, heteroaryl and —CF$_3$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benzenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

Compounds of the Invention

In a first aspect of the present invention there is provided a compound of formula (I):

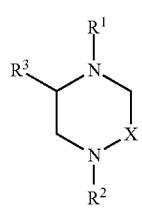

(I)

wherein

X is —CHR$^4$—, —CH$_2$CHR$^4$— or —C(=O)—;
R$^1$ is —C(=O)CHR$^5$R$^6$, —C(=O)NR$^5$R$^6$, —C(=O)CH$_2$CHR$^5$R$^6$, —C(=O)CH=CR$^5$R$^6$, —C(=S)CHR$^5$R$^6$, —C(=S)NR$^5$R$^6$, —C(=S)CH$_2$CHR$^5$R$^6$, —C(=S)CH=CR$^5$R$^6$, —C(=NR$^7$)CHR$^5$R$^6$, —C(=NR$^7$)NR$^5$R$^6$, —C(=NR$^7$)CH$_2$CHR$^5$R$^6$ or —C(=NR$^7$)CH=CR$^5$R$^6$;

R$^2$ is —C$_{1-6}$alkyl, —C$_{2-6}$alkenyl, —C$_{2-6}$alkynyl, —C(=O)R$^8$, —C(=O)NHR$^7$, —SO$_2$N(R$^7$)$_2$, —W-cycloalkyl, —W-cycloalkenyl, —W-aryl, —W-heterocyclyl, —W-heteroaryl, —W—Z—Y-cycloalkyl, —W—Z—Y-cycloalkenyl, —W—Z—Y-aryl, —W—Z—Y-heterocyclyl or —W—Z—Y-heteroaryl;

R$^3$ is a carboxylic acid, —CH$_2$CO$_2$H, —C(=O)C(=O)OH, —CH$_2$OH, —C(=O)NH$_2$, —CH$_2$C(=O)NH$_2$, —CN, —CH$_2$CN, a carboxylic acid bioistere or a —CH$_2$-carboxylic acid bioisotere;

R$^4$ is hydrogen or together with R$^2$ forms a fused cycloalkyl, cycloalkenyl, aryl, heterocyclyl or heteroaryl ring optionally substituted with one or two substituents selected from —C$_{1-6}$alkyl, —C$_{2-6}$alkenyl, —C$_{2-6}$alkynyl, cycloalkyl, cycloalkenyl, aryl, heterocyclyl, heteroaryl, —C$_{1-6}$alkyleneR$^9$, —C$_{2-6}$alkenyleneR$^9$, —C$_{2-6}$alkynyleneR$^9$, —OC$_{0-6}$alkyleneR$^9$, —OC$_{2-6}$alkenyleneR$^9$, —OC$_{2-6}$alkynyleneR$^9$, —C(=O)C$_{0-6}$alkyleneR$^9$, —C(=O)C$_{2-6}$alkenyleneR$^9$, —C(=O)C$_{2-6}$alkynyleneR$^9$, —C(=O)OC$_{0-6}$alkyleneR$^9$, —C(=O)OC$_{2-6}$alkenyleneR$^9$, —C(=O)OC$_{2-6}$alkynyleneR$^9$, —SO$_2$NHC$_{0-6}$alkyleneR$^9$, —SO$_2$NHC$_{2-6}$alkenyleneR$^9$, —SO$_2$NHC$_{2-6}$alkynyleneR$^9$, —NHSO$_2$C$_{0-6}$alkyleneR$^9$, —NHSO$_2$C$_{2-6}$alkenyleneR$^9$, —NHSO$_2$C$_{2-6}$alkynyleneR$^9$, —NH(=O)NHR$^{10}$, —NHC(=O)OR$^{10}$ or —CH(OH)CH(OH)R$^{10}$;

R$^5$ and R$^6$ are independently selected from hydrogen, —C$_{1-6}$alkyl, —C$_{2-6}$alkenyl, —C$_{2-6}$alkynyl, cycloalkyl, cycloalkenyl, aryl, heterocyclyl, heteroaryl, —CH$_2$cycloalkyl, —CH$_2$cycloalkenyl, —CH$_2$aryl, —CH$_2$heterocyclyl and —CH$_2$heteroaryl; provided that both R$^5$ and R$^6$ are not hydrogen;

R$^7$ is hydrogen, —C$_{1-6}$alkyl, aryl or —C$_{1-6}$alkylenearyl;
R$^8$ is —C$_{1-6}$alkyl, —C$_{2-6}$alkenyl, —C$_{2-6}$alkynyl, aryl or —C$_{1-6}$alkylenearyl;
R$^9$ is cycloalkyl, cycloalkenyl, aryl, heterocyclyl, heteroaryl;
R$^{10}$ is —C$_{1-6}$alkyl, —C$_{2-6}$alkenyl, —C$_{2-6}$alkynyl, cycloalkyl, cycloalkenyl, aryl, heterocyclyl or heteroaryl;
W is a covalent bond, —SO—, —SO$_2$— —C(=O)—, —C(=O)N(R$^7$)—, —C$_{1-4}$alkylene-, —C$_{2-4}$alkenylene-, —C$_{2-4}$alkynylene-, —C$_{1-3}$alkyleneQC$_{1-3}$alkylene-, —C$_{1-4}$alkyleneQ-, —C$_{2-4}$alkenyleneQ- or —C$_{2-4}$alkynyleneQ-;
Z is -cycloalkyl-, -cycloalkenyl-, -aryl-, -heterocyclyl- or -heteroaryl-;
Y is a covalent bond, —O—, —S—, —SO—, —SO$_2$— —N(R$^7$)—, —C(=O)—, —N(R$^7$)C(=O)—, —C(=O)N(R$^7$)—, —C$_{1-3}$alkylene-, —C$_{2-3}$alkenylene-, —C$_{2-3}$alkynylene-; —C$_{1-3}$alkyleneQC$_{1-3}$alkylene-, -QC$_{1-4}$alkylene-, -QC$_{2-4}$alkenylene-, -QC$_{2-4}$alkynylene-, —C$_{2-4}$alkenyleneQ-, —C$_{2-4}$alkynyleneQ-, -QC$_{1-4}$alkyleneQ-, -QC$_{2-4}$alkenyleneQ- or -QC$_{2-4}$alkynyleneQ-; and
Q is —O—, —SO—, —SO$_2$— —N(R$^7$)—, —C(=O)—, —N(R$^7$)C(=O)— or —C(=O)N(R$^7$)—;
wherein each cycloalkyl, cycloalkenyl, aryl, heterocyclyl and heteroaryl is optionally substituted;
or a pharmaceutically acceptable salt thereof.

In some embodiments of the present invention, the compound of formula (I) is a compound of formula (IA):

(IA)

wherein
X is —CHR⁴—, —CH₂CHR⁴— or —C(═O)—;
R¹ is —C(═O)CHR⁵R⁶, —C(═O)NR⁵R⁶, —C(═O)CH₂CHR⁵R⁶, —C(═O)CH═CR⁵R⁶, —C(═S)CHR⁵R⁶, —C(═S)NR⁵R⁶, —C(═S)CH₂CHR⁵R⁶, —C(═S)CHR⁵R⁶, —C(═NR⁷)CHR⁵R⁶, —C(═NR⁷)NR⁵R⁶, —C(═NR⁷)CH₂CHR⁵R⁶ or —C(═NR⁷)CHR⁵R⁶;
R² is —C₁₋₆alkyl, —C₂₋₆alkenyl, —C₂₋₆alkynyl, —C(═O)R⁵, —C(═O)NHR⁷, —SO₂N(R⁷)₂, —W-cycloalkyl, —W-cycloalkenyl, —W-aryl, —W-heterocyclyl, —W-heteroaryl, —W—Z—Y-cycloalkyl, —W—Z—Y-cycloalkenyl, —W—Z—Y-aryl, —W—Z—Y-heterocyclyl or —W—Z—Y-heteroaryl;
R³ is a carboxylic acid, —CH₂CO₂H, —C(═O)C(═O)OH or a carboxylic acid bioisotere;
R⁴ is hydrogen or together with R² forms a fused cycloalkyl, cycloalkenyl, aryl, heterocyclyl or heteroaryl ring optionally substituted with one or two substituents selected from —C₁₋₆alkyl, —C₂₋₆alkenyl, —C₂₋₆alkynyl, cycloalkyl, cycloalkenyl, aryl, heterocyclyl, heteroaryl, —C₁₋₆alkyleneR⁹, —C₂₋₆alkenyleneR⁹, —C₂₋₆alkynyleneR⁹, —OC₀₋₆alkyleneR⁹, —OC₂₋₆alkenyleneR⁹, —OC₂₋₆alkynyleneR⁹, —C(═O)C₀₋₆alkyleneR⁹, —C(═O)C₂₋₆alkenyleneR⁹, —C(═O)C₂₋₆alkynyleneR⁹, —C(═O)OC₀₋₆alkyleneR⁹, —C(═O)OC₂₋₆alkenyleneR⁹, —C(═O)OC₂₋₆alkynyleneR⁹, —SO₂NHC₀₋₆alkyleneR⁹, —SO₂NHC₂₋₆alkenyleneR⁹, —SO₂NHC₂₋₆alkynyleneR⁹, —NHSO₂C₀₋₆alkyleneR⁹, —NHSO₂C₂₋₆alkenyleneR⁹, —NHSO₂C₂₋₆alkynyleneR⁹, —NH(═O)NHR¹⁰, —NHC(═O)OR¹⁰ or —CH(OH)CH(OH)R¹⁰;
R⁵ and R⁶ are independently selected from hydrogen, —C₁₋₆alkyl, —C₂₋₆alkenyl, —C₂₋₆alkynyl, cycloalkyl, cycloalkenyl, aryl, heterocyclyl, heteroaryl, —CH₂cycloalkyl, —CH₂cycloalkenyl, —CH₂aryl, —CH₂heterocyclyl and —CH₂heteroaryl; provided that both R⁵ and R⁶ are not hydrogen;
R⁷ is hydrogen, —C₁₋₆alkyl, aryl or —C₁₋₆alkylenearyl;
R⁸ is —C₁₋₆alkyl, —C₂₋₆alkenyl, —C₂₋₆alkynyl, aryl or —C₁₋₆alkylenearyl;
R⁹ is cycloalkyl, cycloalkenyl, aryl, heterocyclyl, heteroaryl;
R¹⁰ is —C₁₋₆alkyl, —C₂₋₆alkenyl, —C₂₋₆alkynyl, cycloalkyl, cycloalkenyl, aryl, heterocyclyl or heteroaryl;
W is a covalent bond, —SO—, —SO₂— —C(═O)—, —C(O)N(R⁷)—, —C₁₋₄alkylene-, —C₂₋₄alkenylene-, —C₂₋₄alkynylene-, —C₁₋₃alkyleneQC₁₋₃alkylene-, —C₁₋₄alkyleneQ-, —C₂₋₄alkenyleneQ- or —C₂₋₄alkynyleneQ-;
Z is -cycloalkyl-, -cycloalkenyl-, -aryl-, -heterocyclyl- or -heteroaryl-;
Y is a covalent bond, —O—, —S—, —SO—, —SO₂— —N(R⁷)—, —C(═O)—, —N(R⁷)C(═O)—, —C(═O)N(R⁷)—, —C₁₋₃alkylene-, —C₂₋₃alkenylene-, —C₂₋₃alkynylene-, —C₁₋₃alkyleneQC₁₋₃alkylene-, -QC₁₋₄alkylene-, -QC₂₋₄alkenylene-, -QC₂₋₄alkynylene-, —C₁₋₄alkyleneQ-, —C₂₋₄alkenyleneQ-, —C₂₋₄alkynyleneQ-, -QC₁₋₄alkyleneQ-, -QC₂₋₄alkenyleneQ- or -QC₂₋₄alkynyleneQ-; and
Q is —O—, —S—, —SO—, —SO₂— —N(R⁷)—, —C(═O)—, —N(R⁷)C(═O)— or —C(═O)N(R⁷)—;
wherein each cycloalkyl, cycloalkenyl, aryl, heterocyclyl and heteroaryl is optionally substituted;
or a pharmaceutically acceptable salt thereof.

In particular embodiments of formula (I), one or more of the following applies:
X is —CHR⁴—, especially —CH₂—;
R¹ is —C(═O)CHR⁵R⁶, —C(═O)NR⁵R⁶, especially —C(═O)CH(aryl)(aryl), —C(═O)CH(aryl)(cycloalkyl), —C(═O)CH(cycloalkyl)(cycloalkyl), —C(═O)N(aryl)(aryl), —C(═O)N(aryl)(cycloalkyl) or —C(═O)N(cycloalkyl)(cycloalkyl), more especially —C(═O)CH(phenyl)(phenyl), —C(═O)CH(phenyl)(cyclohexyl), —C(═O)CH(cyclohexyl)(cyclohexyl), —C(═O)N(phenyl)(phenyl), —C(═O)N(phenyl)(cyclohexyl) or —C(═O)N(cyclohexyl)(cyclohexyl), even more especially —C(═O)CH(phenyl)(phenyl) or —C(═O)N(phenyl)(phenyl), most especially —C(═O)CH(phenyl)(phenyl);
R² is —C₁₋₆alkyl, —C₂₋₆alkenyl, cycloalkyl, cycloalkenyl, aryl, heterocyclyl, heteroaryl, heterocyclylaryl, —C₁₋₄alkylenecycloalkyl, —C₁₋₄alkylenecycloalkenyl, —C₁₋₄alkylenearyl, —C₁₋₄alkyleneheterocyclyl, —C₁₋₄alkyleneheteroaryl, —C₂₋₄alkenylenecycloalkyl, —C₂₋₄alkenylenecycloalkenyl, —C₂₋₄alkenylenearyl, —C₂₋₄alkenyleneheterocyclyl, —C₂₋₄ alkenyleneheteroaryl, —C₂₋₄alkynylenecycloalkyl, —C₂₋₄alkynylenecycloalkenyl, —C₂₋₄alkynylenearyl, —C₂₋₄alkynyleneheterocyclyl, —C₂₋₄alkynyleneheteroaryl, -heterocyclylaryl, -heteroarylaryl, -heterocyclylC₁₋₃alkylenearyl, —C₁₋₃alkyleneheterocyclylaryl, —C₁₋₃alkyleneheteroarylaryl —CH₂C(═O)NHCH₂cycloalkyl, —CH₂C(═O)NHCH₂cycloalkenyl, —CH₂C(═O)NHCH₂aryl, —CH₂C(═O)NHCH₂heterocyclyl, —CH₂C(═O)NHCH₂heteroaryl, —C(═O)NHC₁₋₃alkylenecycloalkyl, —C(═O)NHC₁₋₃alkylenecycloalkenyl, —C(═O)NHC₁₋₃alkylenearyl, —C(═O)NHC₁₋₃alkyleneheterocyclyl, —C(═O)NHC₁₋₃alkyleneheteroaryl, —CH₂SO₂C₁₋₃alkylenecycloalkyl, —CH₂SO₂C₁₋₃alkylenecycloalkenyl, —CH₂SO₂C₁₋₃alkylenearyl, —CH₂SO₂C₁₋₃alkyleneheterocyclyl, —CH₂SO₂C₁₋₃alkyleneheteroaryl, —CH₂OC₁₋₃alkylenecycloalkyl, —CH₂OC₁₋₃alkylenecycloalkenyl, —CH₂OC₁₋₃alkylenearyl, —CH₂OC₁₋₃alkyleneheterocyclyl or —CH₂OC₁₋₃alkyleneheteroaryl; especially. —C₁₋₆alkyl, —C₂₋₆alkenyl, -cycloalkyl, -cycloalkenyl, -aryl, -heterocyclyl, -heteroaryl, —C₁₋₄alkylenecycloalkyl, —C₁₋₄alkylenecycloalkenyl, —C₁₋₄alkylenearyl, —C₁₋₄alkyleneheterocyclyl, —C₁₋₄alkyleneheteroaryl, —C₂₋₄alkenylenecycloalkyl, —C₂₋₄alkenylenecycloalkenyl, —C₂₋₄alkenylenearyl, —C₂₋₄alkenyleneheterocyclyl, —C₂₋₄alkenyleneheteroaryl, -heterocyclylaryl, -heteroarylaryl, -heterocyclylC₁₋₃alkylenearyl, -heteroarylC₁₋₃alkylenearyl, —C₁₋₃alkyleneheterocyclylaryl, or —C₁₋₃alkyleneheteroarylaryl, wherein each cycloalkyl, cycloalkenyl, aryl, heterocyclyl and heteroaryl is optionally substituted with one or two substituents selected from —C₁₋₆alkyl, —OC₁₋₆alkyl or -halo; especially where R² is phenyl, benzyl, —CH₂CH₂phenyl, —CH₂CH═CH-phenyl, —CH₂C≡C-phenyl, —CH₂C≡C-4-fluoro-phenyl, —CH₂CH₂C≡Cphenyl, —CH₂CH₂C≡C-4-fluorophenyl, —CH₂CH₂CH₂phenyl, -2-methylbutyl, -5-(3-methyl-1-phenylpyrazole), -3-(1,5-diphenylpyrazole), -3-(5-phenylpyrazole), -3-(5-methyl-1-phenylpyrazole), 3-(5-(1-methylethyl)-1-phenylpyrazole, -2-(5-phenyloxazole), -5-(5-benzyloxazole), -5-(1-benzyl-3-methylpyrazole), -benzyl-5-methylpyrazole, —CH₂-4-(2-phenyloxazole), -5-(1-benzyl)-3-trifluoromethylpyrazole and -5-(1-benzyl-3-methylpyrazole);
R³ is —CO₂H, —CH₂CO₂H, —C(═O)C(═O)OH, —C(═O)NH₂, —CN, —C(═O)NHSO₂C₁₋₆alkyl, —C(═O)NHSO₂phenyl, —C(═O)NHSO₂N(C₁₋₆alkyl)₂ or —C(═O)NHSO₂CF₃, especially —CO₂H, —CH₂CO₂H, —C(═O)NHSO₂C₁₋₄alkyl, —C(═O)NHSO₂N(C₁₋₃alkyl)₂, —C(═O)NHSO₂phenyl or —C(═O)NHSO₂CF₃, more especially —CO₂H;
R⁴ is hydrogen or R⁴ and R² together form a fused aryl, heterocyclyl or heteroaryl ring optionally substituted with one or two substituents selected from -aryl, —C₁₋₃alkylenearyl, —Oaryl, —OC₁₋₃alkylenearyl and —C(═O)OC₁₋₃ alkylenearyl; especially a fused heterocyclyl or heteroaryl ring optionally substituted with phenyl, benzyl, —Obenzyl, or —CO$_2$benzyl;
$R^5$ and $R^6$ are independently selected from phenyl and cyclohexyl, especially where both $R^5$ and $R^6$ are phenyl;
$R^7$ is hydrogen, methyl, ethyl or phenyl.

In some embodiments, $R^3$ has an S stereochemistry.

In one embodiment, the compound of formulae (I) or (IA) is a compound of formula (II):

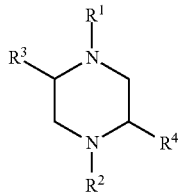

wherein
$R^1$ is —C(=O)CHR$^5$R$^6$, —C(=O)NR$^5$R$^6$, —C(O)CH$_2$CHR$^5$R$^6$, —C(=O)CH=CR$^5$R$^6$, —C(=S)CHR$^5$R$^6$, —C(=S)NR$^5$R$^6$, —C(=S)CH$_2$CHR$^5$R$^6$, —C(=S)CH=CR$^5$R$^6$, —C(=NR$^7$)CHR$^5$R$^6$, —C(=NR$^7$)NR$^5$R$^6$, —C(=NR$^7$)CH$_2$CHR$^5$R$^6$ or —C(=NR$^7$)CH=CR$^5$R$^6$;
$R^2$ is —C$_{1-6}$alkyl, —C$_{2-6}$alkenyl, —C$_{2-6}$alkynyl, —C(=O)R$^8$, —C(=O)NHR$^7$, —SO$_2$N(R$^7$)$_2$, —W-cycloalkyl, —W-cycloalkenyl, —W-aryl, —W-heterocyclyl, —W-heteroaryl, —W—Z—Y-cycloalkyl, —W—Z—Y-cycloalkenyl, —W—Z—Y-aryl, —W—Z—Y-heterocyclyl or —W—Z—Y-heteroaryl; $R^3$ is a carboxylic acid, —CH$_2$CO$_2$H, —C(=O)C(=O)OH, —C(=O)NH$_2$, —CN or a carboxylic acid bioisotere;
$R^4$ is hydrogen or together with $R^2$ forms a fused cycloalkyl, cycloalkenyl, aryl, heterocyclyl or heteroaryl ring optionally substituted with one or two substituents selected from —C$_{1-6}$alkyl, —C$_{2-6}$alkenyl, cycloalkyl, cycloalkenyl, aryl, heterocyclyl, heteroaryl, —C$_{1-6}$alkyleneR$^9$, —C$_{2-6}$alkenyleneR$^9$, —C$_{2-6}$alkynyleneR$^9$, —OC$_{0-6}$alkyleneR$^9$, —OC$_{2-6}$alkenyleneR$^9$, —OC$_{2-6}$alkynyleneR$^9$, —C(=O)C$_{0-6}$alkyleneR$^9$, —C(=O)C$_{2-6}$alkenyleneR$^9$, —C(=O)C$_{2-6}$alkynyleneR$^9$, —C(=O)OC$_{0-6}$alkyleneR$^9$, —C(=O)OC$_{2-6}$alkenyleneR$^9$, —C(=O)OC$_{2-6}$alkynyleneR$^9$, —SO$_2$NHC$_{0-6}$alkyleneR$^9$, —SO$_2$NHC$_{2-6}$alkenyleneR$^9$, —SO$_2$NHC$_{2-6}$alkynyleneR$^9$, —NHSO$_2$C$_{0-6}$alkyleneR$^9$, —NHSO$_2$C$_{2-6}$alkenyleneR$^9$, —NHSO$_2$C$_{2-6}$alkynyleneR$^9$, —NH(=O)NHR$^{10}$, —NHC(=O)OR$^{10}$ or —CH(OH)CH(OH)R$^{10}$;
$R^5$ and $R^6$ are independently selected from hydrogen, —C$_{1-6}$alkyl, —C$_{2-6}$alkenyl, cycloalkyl, cycloalkenyl, aryl, heterocyclyl, heteroaryl, —CH$_2$cycloalkyl, —CH$_2$cycloalkenyl, —CH$_2$aryl, —CH$_2$heterocylyl and —CH$_2$heteroaryl; provided that both $R^5$ and $R^6$ are not hydrogen;
$R^7$ is hydrogen, —C$_{1-6}$alkyl, aryl or —C$_{1-6}$alkylenearyl;
$R^8$ is —C$_{1-6}$alkyl, —C$_{2-6}$alkenyl, —C$_{2-6}$alkynyl, aryl or —C$_{1-6}$alkyleneary;
$R^9$ is cycloalkyl, cycloalkenyl, aryl, heterocyclyl, heteroaryl;
$R^{10}$ is —C$_{1-6}$alkyl, —C$_{2-6}$alkenyl, —C$_{2-6}$alkynyl, cycloalkyl, cycloalkenyl, aryl, heterocyclyl or heteroaryl;
W is a covalent bond, —SO—, —SO$_2$— —C(=O)N(R$^7$)—, —C$_{1-4}$alkylene-, —C$_{2-4}$alkenylene-, —C$_{2-4}$alkynylene-, —C$_{1-3}$alkyleneQC$_{1-3}$alkylene-, —C$_{1-4}$alkyleneQ-, —C$_{2-4}$alkenyleneQ- or —C$_{2-4}$alkynyleneQ-;
Z is -cycloalkyl-, -cycloalkenyl-, -aryl-, -heterocyclyl- or -heteroaryl-;
Y is a covalent bond, —O—, —S—, —SO—, —SO$_2$— —N(R$^7$)—, —C(=O)—, —N(R$^7$)C(=O)—, —C(=O)N(R$^7$)—, —C$_{1-3}$alkylene-, —C$_{2-3}$alkenylene-, —C$_{2-3}$alkynylene-, —C$_{1-3}$alkyleneQC$_{1-3}$alkylene-, -QC$_{1-4}$alkylene-, -QC$_{2-4}$alkenylene-, -QC$_{2-4}$alkynylene-, —C$_{1-4}$alkyleneQ-, —C$_{2-4}$alkenyleneQ-, —C$_{2-4}$alkynyleneQ-, -QC$_{1-4}$alkyleneQ-, -QC$_{2-4}$alkenyleneQ- or -QC$_{2-4}$alkynyleneQ-; and
Q is —O—, —S—, —SO—, —SO$_2$— —N(R$^7$)C(=O)— or —C(=O)N(R$^7$)—;
wherein each cycloalkyl, cycloalkenyl, aryl, heterocyclyl and heteroaryl is optionally substituted;
or a pharmaceutically acceptable salt thereof.

Particular compounds of formula (I) are:

| Compound | X | $R^1$ | $R^2$ | $R^3$ | $R^4$ | $R^2/R^4$ |
|---|---|---|---|---|---|---|
| 1 | —CHR$^4$— | —C(O)CH(phenyl)$_2$ | — | —CO$_2$H (S) | — | ![triazole-CO-O-CH2-Ph] |
| 2 | —CHR$^4$— | —C(O)CH(phenyl)$_2$ | — | —CO$_2$H (S) | — | ![triazole-O-CH2-Ph] |
| 3 | —CHR$^4$— | —C(O)CH(phenyl)$_2$ | — | —CO$_2$H (S) | — | ![imidazole-CH2-Ph] |
| 4 | —CHR$^4$— | —C(O)CH(phenyl)$_2$ | -phenyl | —CO$_2$H (S) | H | — |
| 5 | —CHR$^4$— | —C(O)CH(phenyl)$_2$ | —CH$_2$phenyl | —CO$_2$H (S) | H | — |
| 6 | —CHR$^4$— | —C(O)CH(phenyl)$_2$ | -3-(1,5-diphenyl-pyrazole) | —CO$_2$H (S) | H | — |
| 7 | —CHR$^4$— | —C(O)CH(phenyl)$_2$ | -5-(3-methyl-1-phenyl-pyrazole) | —CO$_2$H (S) | H | — |

-continued

| Compound | X | $R^1$ | $R^2$ | $R^3$ | $R^4$ | $R^2/R^4$ |
|---|---|---|---|---|---|---|
| 8  | —CHR$^4$— | —C(O)CH(phenyl)$_2$ | —CH$_2$CH$_2$phenyl | —CO$_2$H (S) | H | — |
| 9  | —CHR$^4$— | —C(O)CH(phenyl)$_2$ | —CH$_2$CH=CHphenyl | —CO$_2$H (S) | H | — |
| 10 | —CHR$^4$— | —C(O)CH(phenyl)$_2$ | —CH$_2$CH$_2$CH$_2$phenyl | —CO$_2$H (S) | H | — |
| 11 | —CHR$^4$— | —C(O)CH(phenyl)$_2$ | -3-(1-phenylpyrazole) | —CO$_2$H (S) | H | — |
| 12 | —CHR$^4$— | —C(O)CH(phenyl)$_2$ | -3-(5-methyl-1-phenyl-pyrazole) | —CO$_2$H (S) | H | — |
| 13 | —CHR$^4$— | —C(O)CH(phenyl)$_2$ | -3-(5-(1-methytethyl)-1-phenylpyrazole | —CO$_2$H (S) | H | — |
| 14 | —CHR$^4$— | —C(O)CH(phenyl)$_2$ | -2-(5-phenyl-1,3-oxazole) | —CO$_2$H (S) | H | — |
| 15 | —CHR$^4$— | —C(O)CH(phenyl)$_2$ | -2-(5-benzyl-1,3-oxazole) | —CO$_2$H (S) | H | — |
| 16 | —CHR$^4$— | —C(O)CH(phenyl)$_2$ | -5-(1-benzyl-3-methyl-pyrazole) | —CO$_2$H (S) | H | — |
| 17 | —CHR$^4$— | —C(O)CH(phenyl)$_2$ | -3-(1-benzyl-5-methyl-pyrazole) | —CO$_2$H (S) | H | — |
| 18 | —CHR$^4$— | —C(O)CH(phenyl)$_2$ | -2-methylbutyl | —CO$_2$H (S) | H | — |
| 19 | —CHR$^4$— | —C(O)CH(phenyl)$_2$ | —CH$_2$-4-(2-phenyl-1,3-oxazole) | —CO$_2$H (S) | H | — |
| 20 | —CH$_2$CHR$^4$— | —C(O)CH(phenyl)$_2$ | —CH$_2$CH$_2$phenyl | —CO$_2$H (S) | H | — |
| 21 | —CH$_2$CHR$^4$— | —C(O)CH(phenyl)$_2$ | — | —CO$_2$H (S) | — | 2-methyl-4-phenylpiperazinyl (structure) |
| 22 | —CHR$^4$— | —C(O)CH(phenyl)$_2$ | — | —CO$_2$H (S) | — | 1-methyl-2-methyl-5-benzylimidazolyl (structure) |
| 23 | —CHR$^4$— | —C(O)CH(phenyl)$_2$ | -5-(1-benzyl)-3-trifluoromethylpyrazolyl | —CO$_2$H (S) | H | — |
| 24 | —CHR$^4$— | —C(O)CH(phenyl)$_2$ | —CH$_2$C≡C-phenyl | —CO$_2$H (S) | H | — |
| 25 | —CHR$^4$— | —C(O)CH(phenyl)$_2$ | —CH$_2$C≡C-4-fluorophenyl | —CO$_2$H (S) | H | — |
| 26 | —CHR$^4$— | —C(O)CH(phenyl)$_2$ | —CH$_2$CH$_2$C≡C-phenyl | —CO$_2$H (S) | H | — |
| 27 | —CHR$^4$— | —C(O)CH(phenyl)$_2$ | —CH$_2$CH$_2$C≡C-4-fluorophenyl | —CO$_2$H (S) | H | — |
| 28 | —CHR$^4$— | —C(O)CH(phenyl)$_2$ | -5-(1-benzyl)-3-methyl-pyrazolyl | —CONHSO$_2$N(CH$_3$)$_2$ | H | — |

*indicates the shared bond between the fused ring and the piperazine ring.

Particular compounds of the formula (I) include compounds 4, 5, 6, 7, 8, 9, 10, 16, 23, 24, 25 and 26, especially compounds 4, 5, 7, 10, 16 and 23.

In some embodiments, the compounds of formula (I) are selective AT$_2$ receptor antagonists. In particular embodiments, the selective AT$_2$ receptor antagonists have an IC$_{50}$ at the AT$_2$ receptor of ≤100 nM and an IC$_{50}$ at the AT$_1$ receptor of >100,000 nM (10 μM) using the assay methodologies described in Biological Examples 1 and 2.

The compounds of the invention are made by methods known in the art from commercially available starting materials.

For preparation of the piperazine compounds, a suitable starting material is 1N-protected-piperazine-2-carboxylic acid or its methyl ester, the enantiomers of which are commercially available.

R$^1$ may be introduced either before the introduction of R$^2$ or after the introduction of R$^2$, or after formation of the fused heterocyclyl or heteroaryl ring. If R$^2$ is introduced prior to the introduction of R$^1$, it may be necessary to protect the ring nitrogen during the alkylation reaction. Suitable nitrogen protecting groups are known in the art, for example, in Greene & Wutz, Protective Groups in Organic Synthesis, Third Edition, John Wiley & Sons, 1999. A suitable nitrogen protecting group is t-butoxycarbonyl (Boc).

R$^1$ may be introduced by amide formation with a suitable carboxylic acid and the ring nitrogen. Amide formation is well known in the art and may involve the activation of the carboxylic acid, for example, the carboxy group is activated by formation of an acid chloride, carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCI), 1-hydroxybenzotriazole (HOBt), 1-hydroxy-7-azabenzotriazole (HOAt), ethyl-2-cyano-2-cyano-2-(hydroxyimino)acetate (Oxyma Pure), O-benzotriawle-N,N,N',N'-tetramethyluronium hexafluorophosphate (HBTU), O-(7-azabenzotriazol-1-yl)-N,N,N',N'-tetramethyluronium hexafluorophosphate (HATU), 0-(6-chloro-1H-benzotriazol-1-yl)-1,1,3,3-tetramethyluronium tetrafluorophosphate (HCTU), 0-benzotriazol-1-yl-N,N,N'N'-tetramethyluronium tetrafluoroborate (TBTU), (benzotriazol-1-yloxy)tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

R$^2$ may be introduced by alkylation or arylation reactions as known in the art. For example, an alkylhalide or arylalkylhalide may be used to alkylate the unprotected piperazine nitrogen atom. An aryl group may be directly bonded to the unprotected piperazine nitrogen, for example, by copper catalysed arylation using an arylboronic acid in the presence of a copper catalyst such as copper diacetate (Cu(OAc)$_2$).

When $R^2$ is a heteroaryl or heterocyclyl group it may be introduced directly by means of an appropriate halide or heteroaryl boronic acid or may be prepared in situ. For example, the unprotected piperazine nitrogen may be alkylated with a suitably functionalized alkyl or alkylaryl group, for example, to provide a 1,3-diketobutyl substituent or a 3-phenyl-3-keto-1-thiomethyl-1-propenyl substituent. Addition of a hydrazine or a substituted hydrazine gives a pyrazole substituent as $R^2$.

Where $R^2$ forms an amide with the piperazine ring nitrogen atom, $R^2$ may be introduced by methods known for amide formation, such as those described for introduction of $R^1$.

Fused ring systems may also be readily prepared by literature procedures. For example, imidazo[1,2-a]piperazine carboxylic acids and triazolo[4,3-a]piperazine carboxylic acids may be prepared from suitable N-protected piperazine carboxylic acid imino ethers by reaction with substituted or unsubstituted propargylamine or ethynylamine or acetic hydrazide or aroylhydrazide respectively [McCort & Pascal, *Tet. Lett.*, 1992, 33(31):4443-4446 and WO 2009/158394].

Alternatively, a 2-(aminomethyl)pyrazine can be reacted with an aroylchloride such as PhCOCl to provide an aryl amide that is subsequently cyclised with POCl$_3$ to give an aryl substituted imidazo[1,2-a]pyrazine ring system, which may be subsequently reduced with H$_2$ to give an imidazo[1,2-a]piperazine ring system [WO 2009/158394].

Another approach includes alkylation of an imidazole-2-aldehyde with a suitable N-protected 2-hydroxyethylamine. The resulting 5-(2-hydroxyethyl-aminomethyl)imidazole hydroxy group is displaced by chloride using thionyl chloride and ring cyclization occurs to produce an imidazo[1,2-a]piperazine ring system [WO 2009/158394].

Where $R^2$ or substituents on the ring formed by $R^2$ and $R^4$ contain reactive functional groups such as double or triple bonds, hydroxy groups, amines and carboxylic acids, these groups may be manipulated by methods known in the art such as oxidation, reduction, alkylation, halogenation and the like. For example, double bonds may be reduced to alkyl groups or oxidized, for example, with meta-chloro-peroxybenzoic acid (MCPBA) to provide an epoxide. Triple bonds may be reduced stereoselectively to give double bonds with a desired cis or trans stereochemistry. Hydroxy groups may be oxidized to ketones, aldehydes or carboxylic acids.

Similar reactions may be performed using commercially available diazepines such as R- or S-hexahydro-4-[(4-methylphenysulfonyl]-2-oxo-1H-1,4-diazepine-5-carboxylic acid methyl ester, 2-Cbz-8-Boc-decahydropyrazino[1,2-g][1,4]diazepine-7-carboxylic acid and 2-Cbz-decahydropyrazino[1,2-g][1,4]diazepine-7-carboxylic acid.

Methods of the Invention

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an AT$_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several antiretroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barré syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. Examples of disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired neuronal conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired, nerve conduction velocity is associated with Carpel Tunnel Syndrome, ulnar neuropathy, Guillian-Barré Syndrome, fascioscapulohumeral muscular dystrophy and spinal disc herneation.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance travelled. Sensory nerve conduction, is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 μg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include amelioration of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal hypersensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include 5HT$_3$ receptor antagonists such as alosetron (Lotronex®).

The AT$_2$ receptor antagonists of the invention are also useful in combination with radiotherapy in cancer patients.
Compositions of the Invention While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations; the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions may comprise further active ingredients such as other therapies to treat neuropathic or inflammatory pain or the underlying condition that is causing the neuropathic or inflammatory pain or therapies to treat conditions characterized by neuronal hypersensitivity, disorders associated with aberrant nerve regeneration, proliferative disorders or disorders associated with an imbalance between bone resorption and bone formation.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations:

| | |
|---|---|
| DCM | dichloromethane |
| DBAD | dibenzyl azodicarboxylate |
| RT | room temperature |
| PE | petroleum ether |
| EA or EtOAc | ethyl acetate |
| THF | tetrahydrofuran |

| | |
|---|---|
| Et₂O | diethyl ether |
| MeOH | methanol |
| Et₃N | triethylamine |
| DMAP | 4-dimethylaminopyridine |
| DIPEA | N,N-disopropylethylamine |
| Bn | benzyl |
| Bz | benzoyl |
| TLC | thin layer chromatography |
| DABCO | 1,4-diazabicylco[2.2.2]octane |
| DMF | dimethylformamide |
| LR | Lawesson's Reagent |
| TFA | trifluoroacetic acid |
| EDCI | 1-ethyl-3-(3-dimethylaminopropyl)carbodiimide |
| Py | Pyridine |
| EtOH | ethanol |
| Boc | t-butyloxycarbonyl |
| IPA | isopropylalcohol |

General Methods Used in the Synthesis Examples.

LC-MS (Agilent):
1. LC: Agilent Technologies 1200 series, Binary Pump, Diode Array Detector. Ultimate AQ-C18, 3 μm, 2.1×50 mm column. Mobile phase: B (MeOH) and A (0.07% HCOOH aqueous solution). Flow Rate: 0.4 mL/min at 25° C. Detector: 214 nm, 254 nm. Gradient stop time, 5 min. Timetable:

| T (min) | B (%) | A (%) |
|---|---|---|
| 0 | 10 | 90 |
| 0.2 | 10 | 90 |
| 1.2 | 95 | 5 |
| 2.8 | 95 | 5 |
| 3 | 10 | 90 |
| 5 | 10 | 90 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 μg/mL, then filtered through a 0.22 μm filter membrane. Injection volume: 1~10 μL.

LC-MS (Waters):
1. LC: Waters 2695, Quaternary Pump, Waters 2996 Photodiode Array Detector. Xbridge-C18, 3.5 μm, 2.1×50 mm column. Mobile Phase: B (MeOH) and A (0.07% HCOOH aqueous solution). Flow Rate: 0.3 mL/min at 30° C. Detector: 214 nm, 254 nm. Gradient stop time, 10 min. Timetable:

| T (min) | B (%) | A (%) |
|---|---|---|
| 0 | 10 | 90 |
| 2.5 | 75 | 25 |
| 5.0 | 95 | 5 |
| 7.5 | 95 | 5 |
| 7.6 | 10 | 90 |
| 10 | 10 | 90 |

2. MS: Micromass QZ, TIC: 100~900 m/z, Ion Source: ES, Capillary: 3 kV, Cone: 3V, Extractor: 3V, Drying gas flow: 600 L/hr, cone: 50 L/hr, Desolvation temperature: 300° C., Source temperature: 100° C.
3. Sample preparation: samples were dissolved in methanol at 1~10 μg/mL, then filtered through a 0.22 μm filter membrane. Injection volume: 1~10 μL.

LC-MS (Agilent, P-2) (Positive Ion mode) or LC-MS (Agilent, N-2) (Negative Ion Mode):
1. LC: Agilent Technologies 1200 series, Binary Pump, Diode Array Detector. Xbridge-C18, 2.5 μm, 2.1×30 mm column. Mobile phase: B (MeOH) and A (0.07% HCOOH aqueous solution). Flow Rate: 0.5 mL/min at 30° C. Detector: 214 nm, 254 nm. Gradient stop time, 5 min. Timetable:

| T (min) | B (%) | A (%) |
|---|---|---|
| 0 | 80 | 20 |
| 0.2 | 80 | 20 |
| 0.8 | 5 | 95 |
| 2.8 | 5 | 95 |
| 3 | 80 | 20 |
| 5 | 80 | 20 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
1. Sample preparation: samples were dissolved in methanol at 1~10 μg/mL, then filtered through a 0.22 μm filter membrane. Injection volume: 1~10 μL.

LC-MS (Agilent, P-1) (Positive Ion mode) or LC-MS (Agilent, N-1) (Negative Ion mode) (low polarity samples):
1. LC: Agilent Technologies 1200 series, Binary Pump, Diode Array Detector. Xbridge-C18, 2.5 μm, 2.1×30 mm column. Mobile phase: B (MeOH) and A (0.07% HCOOH aqueous solution). Flow Rate: 0.4 mL/min at 30° C. Detector: 214 nm, 254 nm. Gradient stop time, 6 min. Timetable:

| T (min) | B (%) | A (%) |
|---|---|---|
| 0 | 80 | 20 |
| 0.2 | 80 | 20 |
| 0.8 | 5 | 95 |
| 3.8 | 5 | 95 |
| 4 | 80 | 20 |
| 6 | 80 | 20 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 μg/mL, then filtered through a 0.22 μm filter membrane. Injection volume: 1~10 μL.

Analytical HPLC:
1. (Referred to as "Aligent") Agilent Technologies 1200 series, Quaternary Pump, Diode Array Detector. Ultimate AQ-C18, 5 μm, 4.6×250 mm column. Mobile Phase: B (MeOH) and A (0.07% TFA aqueous solution). Flow Rate: 1.00 mL/min at 30° C. Detector: 214 nm, 254 nm. Gradient stop time: 20 min. Timetable:

| T (min) | B (%) | A (%) |
|---|---|---|
| 0 | 40 | 60 |
| 3 | 40 | 60 |
| 5 | 60 | 40 |
| 7 | 80 | 20 |
| 8 | 95 | 5 |
| 15 | 95 | 5 |
| 17 | 40 | 60 |
| 20 | 40 | 60 |

2. Sample preparation: samples were dissolved in methanol at ~1 mg/mL, then filtered through a 0.22 μm filter membrane. Injection volume: 1~10 μL.

Referred to as "JULY-L" or "SYN-001"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 15 min. Timetables:

| Method name: SYN-001 (high polarity) | | |
|---|---|---|
| T (min) | C (%) | D (%) |
| 0 | 5 | 95 |
| 2 | 5 | 95 |
| 5 | 12 | 88 |
| 6 | 40 | 60 |
| 7 | 95 | 5 |
| 10 | 95 | 5 |
| 12 | 60 | 40 |
| 13 | 5 | 95 |
| 15 | 5 | 95 |

| Method name: JULY-L (average and low polarity) | | |
|---|---|---|
| T (min) | C (%) | D (%) |
| 0 | 20 | 80 |
| 2 | 20 | 80 |
| 4 | 40 | 60 |
| 5 | 70 | 30 |
| 6 | 95 | 5 |
| 10 | 95 | 5 |
| 11 | 70 | 20 |
| 12 | 20 | 80 |
| 15 | 20 | 80 |

2. Sample preparation: samples were dissolved in methanol at ~1 mg/mL, then filtered through a 0.22 μm filter membrane. Injection volume: 1~10 μL.

Referred to as "ZSJ-2"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 30 Min. Timetable:

| Method name: ZSJ-2 | | |
|---|---|---|
| T (min) | C (%) | D (%) |
| 0 | 20 | 80 |
| 28 | 95 | 5 |
| 30 | 70 | 30 |

2. Sample preparation: samples were dissolved in methanol at ~1 mg/mL, then filtered through a 0.22 μm filter membrane. Injection volume: 1~10 μL.

Example 1: Compound 4 (S)-1-(2,2-diphenylacetyl)-4-phenylpiperazine-2-carboxylic acid 1. Procedure for the Preparation of 4b

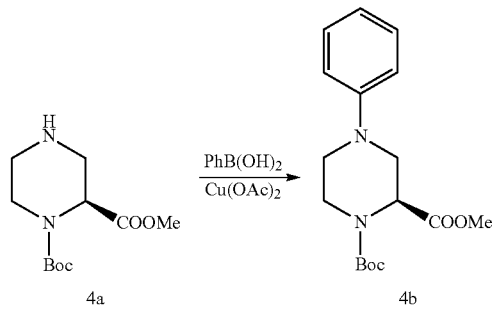 [SMILES: "PhB(OH)2" ; COC(=O)[C@@H]1CNCCN1C(=O)OC(C)(C)C ; COC(=O)[C@@H]1CN(c2ccccc2)CCN1C(=O)OC(C)(C)C ; "Cu(OAc)2"]

To a stirred solution of compound 4a (100 mg, 0.41 mmol) and PhB(OH)$_2$ (75 mg, 0.61 mmol) in DCM (2 mL) was added Cu(OAc)$_2$ (22 mg, 0.12 mmol) at RT and the mixture was stirred overnight, TLC (MeOH:DCM=1:10) showed most of starting material was consumed. The reaction was repeated on a larger batch of compound 4a (1.0 g, 4.1 mmol) and the reaction mixtures were combined and washed with cold water (20 mL) then brine (10 mL×2), dried over Na$_2$SO$_4$, filtered and concentrated in vacuo. The residue was purified by chromatography (EA:PE=1:50) to give 4b (450 mg, 31%) as a colorless oil. LC-MS (Agilent): R$_t$ 3.35 min; m/z calculated for C$_{17}$H$_{24}$N$_2$O$_4$ [M+H]$^+$ 321.2, [M+Na]$^+$ 343.2. found [M+H]$^+$ 321.1, [M+Na]$^+$ 343.1.

2. Procedure for the Preparation of 4c

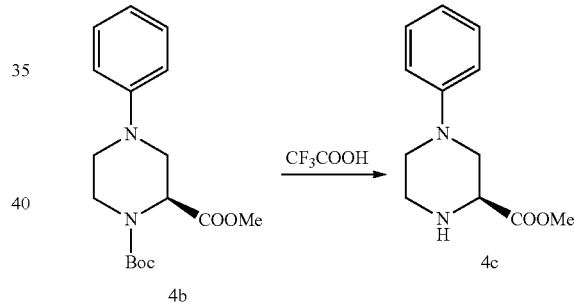

To a stirred solution of 4b (0.45 g, 1.4 mmol) in DCM (5 mL) was added CF$_3$COOH (0.96 g, 8.4 mmol) at RT and the mixture was stirred at RT overnight, TLC (MeOH:DCM=10:1) showed the starting material was consumed. The mixture was concentrated in vacuo, the residue was dissolved in EA (5 mL), washed with a saturated aqueous NaHCO$_3$ solution, brine (3 mL×2), dried over Na$_2$SO$_4$, filtered and concentrated in vacuo to give 4c (280 mg, 90%) as a colorless oil. LC-MS (Agilent): R$_t$ 2.57 min; m/z calculated for C$_{12}$H$_{17}$N$_2$O$_2$ [M+H]$^+$ 221.1. found [M+H]$^+$ 221.1.

3. Procedure for the Preparation of 4d

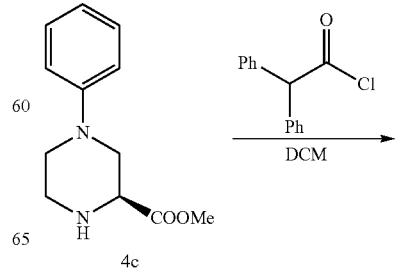

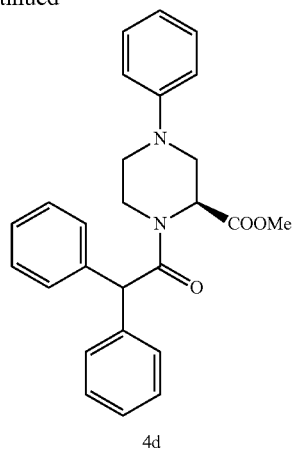

4d

To a stirred solution of 4c (260 mg, 1.18 mmol) and Et₃N (238 mg, 2.36 mmol) in DCM (5 mL) was added diphenylacetyl chloride (408 mg, 1.77 mmol), prepared from diphenylacetic acid and thionyl chloride, at 0° C. and the mixture was stirred at RT for 10 min, TLC (MeOH:DCM=1:10) showed the starting material was consumed. DCM/water (5 mL/10 mL) was added, the organic layer was separated, washed with brine (5 mL×2), dried over Na₂SO₄, filtered and concentrated in vacuo. The residue was purified by chromatography (PE:EA=20:1 to 10:1) to give 4d (350 mg, 71%) as an off-white solid. LC-MS (Agilent): R$_t$ 3.30 min; m/z calculated for C$_{26}$H$_{27}$N$_2$O$_3$ [M+H]$^+$ 415.2, [M+Na]$^+$ 437.2. found [M+H]$^+$ 415.2, [M+Na]$^+$ 437.2.

4. Procedure for the Preparation of 4

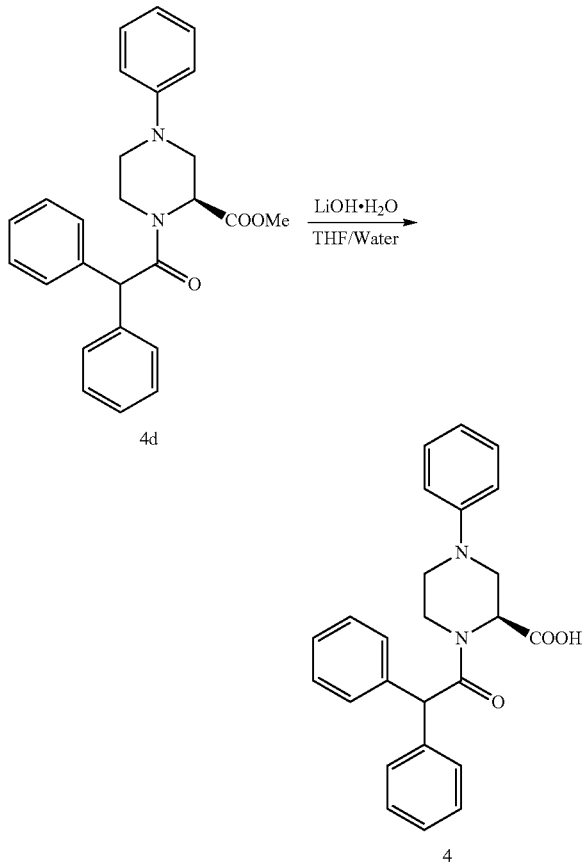

To a stirred solution of 4d (350 mg, 0.84 mmol) in THF (7 mL) was added a solution of LiOH.H₂O (53 mg, 1.27 mmol) in water (3 mL) at 0° C. and the mixture was stirred at RT overnight, TLC (MeOH:DCM=1:10) showed the starting material was consumed. The mixture was concentrated in vacuo to remove most of the THF. The residue was partitioned between EA (3 mL) and water (10 mL) and the mixture acidified to pH 3-4 with 1M HCl. The organic phase was washed with brine (5 mL×2), dried over Na₂SO₄, filtered and concentrated in vacuo. Crude 4 was washed with n-hexane to give pure 4 (280 mg, 82%) as an off-white solid. LC-MS (Agilent): R$_t$ 3.25 min; m/z calculated for C$_{25}$H$_{24}$N$_2$O$_3$ [M+H]$^+$ 401.2, [M+Na]$^+$ 423.2. found [M+H]$^+$ 401.2, [M+Na]$^+$ 423.2. HPLC (214 and 254 nm): R$_t$ 13.53 min.

Example 2: Compound 5 (S)-4-benzyl-1-(2,2-diphenylacetyl)piperazine-2-carboxylic acid 1. Procedure for the Preparation of Compound 5a

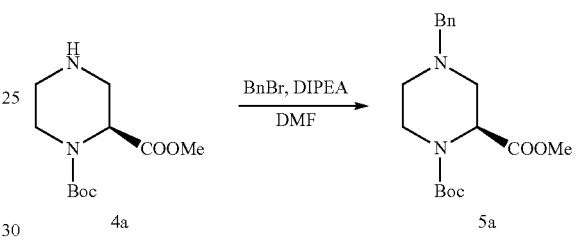

To a solution of 4a (0.5 g, 2.0 mmol) in DMF (10 mL) at 0° C. was added DIPEA (317.4 mg, 2.45 mmol) and benzyl bromide (359.1 mg, 2.1 mmol) and the mixture was stirred at RT for 40 min, TLC (PE:EA=4:1) showed that the starting material was consumed. Water (30 mL) was added and the mixture was extracted with EA (30 mL). The organic extract was washed with brine, dried over Na₂SO₄ and concentrated in vacuo to give 5a (650 mg, 97%) as a yellow oil. LC-MS (Agilent): R$_t$ 3.28 min; m/z calculated for C$_{18}$H$_{26}$H$_2$O$_4$ [M+H]$^+$ 335.1. found [M+H]$^+$ 355.1.

2. Procedure for the Preparation of Compound 5b

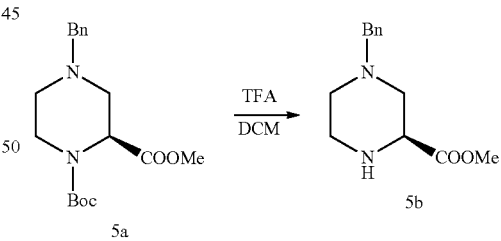

To a solution of 5a (650 mg, 1.95 mmol) in DCM (8 mL) was added TFA (1.34 g, 11.7 mmol) and the mixture was stirred at RT overnight, TLC (PE:EA=4:1) showed that the starting material was consumed. The solvent was removed in vacuo, water (15 mL) and Et₂O (15 mL) were added and the organic layer was separated. The aqueous phase was adjusted to pH 8 with a saturated aqueous Na₂CO₃ solution and extracted with DCM (15 mL×2). The combined organic extracts were washed with brine, dried over Na₂SO₄ and concentrated in vacuo to give 5b (300 mg, 65%) as a yellow oil. LC-MS (Agilent): R$_t$ 0.77 min; m/z calculated for C$_{13}$H$_{18}$N$_2$O$_2$ [M+H]$^+$ 235.1. found [M+H]$^+$ 235.1.

3. Procedure for the Preparation of Compound 5c

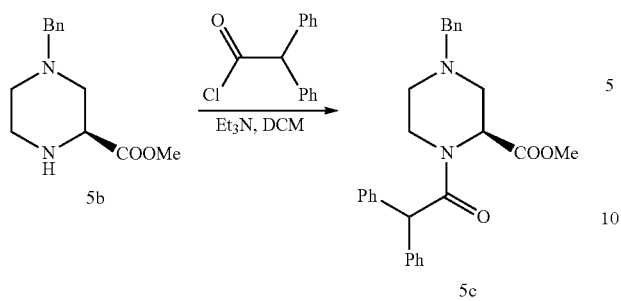

To a solution of compound 5b (300 mg, 1.28 mmol) in DCM (6 mL) was added Et$_3$N (194 mg, 1.92 mmol) and a solution of diphenylacetyl chloride (354 mg, 1.54 mmol) in DCM (2 mL) and the mixture was stirred at RT for 30 min, TLC showed that the starting material was consumed. Water (10 mL) was added, the layers were separated and the aqueous phase was extracted with DCM (10 mL). The combined organic extracts were washed with brine, dried over Na$_2$SO$_4$ and concentrated in vacuo. Purification by silica column (PE:EA=1:0 to 3:1) gave 5c (470 mg 85%) as a white solid. LC-MS (Agilent): R$_t$ 3.30 min; m/z calculated for C$_{27}$H$_{23}$N$_2$O$_3$ [M+H]$^+$ 429.2. found [M+H]$^+$ 429.2.

4. Procedure for the Preparation of 5

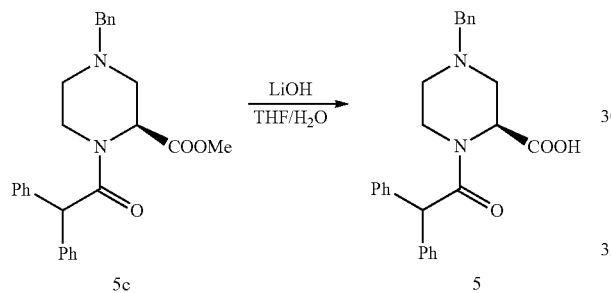

To a solution of compound 5c (250 mg, 0.58 mmol) in THF/water (6 mL/2 mL) was added LiOH (73.5 mg, 1.75 mmol) and the Mixture was stirred at RT overnight, TLC showed that the starting material was consumed. Most of the THF was removed in vacuo, water (20 mL) and Et$_2$O (10 mL) were added and the Et$_2$O phase was removed. DCM (10 mL) was added and the aqueous layer was adjusted to pH 2-3 with a 1 M aqueous HCl solution. The layers were separated and the aqueous layer was extracted with DCM (2×10 mL). The combined organic extracts were washed with brine, dried over Na$_2$SO$_4$ and concentrated in vacuo to give 5 (220 mg, 91%) as a white solid. LC-MS (Agilent): R$_t$ 3.30 min; m/z calculated for C$_{26}$H$_{26}$N$_2$O$_3$ [M+H]$^+$ 415.2. found [M+H]$^+$ 415.2. HPLC (214 and 254 nm): R$_t$ 14.18 min.

Example 3: Compound 6 (S)-4-(1,5-diphenyl-1H-pyrazol-3-yl)-1-(2,2-diphenylacetyl)-piperazine-2-carboxylic acid

1. Procedure for the Preparation of 6b

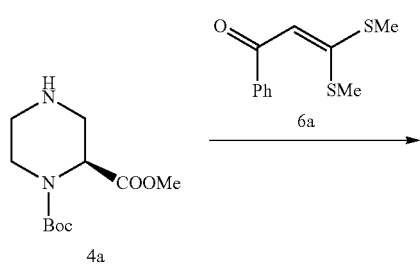

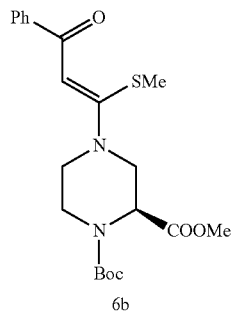

A mixture of the 4a (2.00 g, 13.8 mmol) and 6a (9.34 g, 41.6 mmol) (prepared according to the procedure in *Tetrahedron*, 2010, 66, 2843) in toluene (40 mL) was heated at 130° C. in a sealed tube for 3 hours, TLC (DCM:MeOH=20:1) showed the starting material was consumed. The solvent was removed in vacuo and the residue was purified by Al$_2$O$_3$ column (PE:EA=10:1 to 4:1) to give 6b (600 mg, 16%) as a thick yellow oil. LC-MS (Agilent): R$_t$ 3.27 min; m/z calculated for C$_{21}$H$_{28}$N$_2$O$_5$S [M+H]$^+$ 421.2, [M+Na]$^+$ 443.2. found [M+H]$^+$ 421.2, [M+Na]$^+$ 443.2.

2. Procedure for the Preparation of Compound 6c

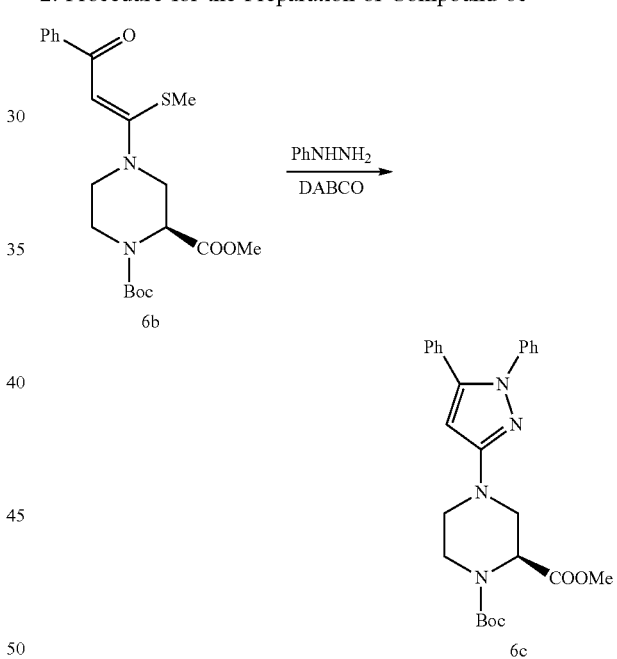

A mixture of 6b (600 mg, 1.42 mmol), DABCO (192 mg, 1.71 mmol) and PhNHNH$_2$ (185 mg, 1.71 mmol) in t-BuOH (30 mL) was heated at reflux overnight, TLC (PE:EtOAc=2:1) showed most of the starting material was consumed. The mixture was cooled to RT and concentrated in vacuo. The residue was dissolved in EA (30 mL) and washed with a 0.1 M aqueous HCl solution (20 mL×2) and brine, then dried over Na$_2$SO$_4$ and concentrated in vacuo. Purification by chromatography (PE:EA=50:1 to 20:1) gave 6c (200 mg, 30%) as a yellow solid. LC-MS (Agilent): R$_t$ 3.44 min; m/z calculated for C$_{26}$H$_{30}$N$_4$O$_4$ [M+H]$^+$ 463.2, [M+Na]$^+$ 485.2, [M+H]$^+$ 463.2, [M+Na]$^+$ 485.2.

3. Procedure for the Preparation of Compound 6d

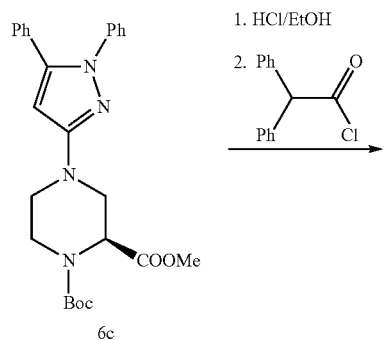

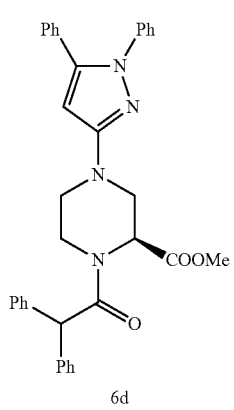

A solution of 6c (200 mg, 0.43 mmol) in 4 M HCl/EtOH (5 mL) was stirred at RT for 3 hours, TLC (PE:EA=4:1) showed the reaction was complete. The mixture was concentrated in vacuo and the residue was partitioned between DCM (20 mL) and water (20 mL). The aqueous layer was basified to pH 7-8 with a saturated aqueous Na$_2$CO$_3$ solution and the layers were separated. The aqueous layer was extracted with DCM (20 mL) and the combined organic extracts were washed with brine (20 mL×1), dried over Na$_2$SO$_4$, and filtered. To the filtrate was added Et$_3$N (53 mg, 0.52 mmol) and diphenylacetyl chloride (109 mg, 0.47 mmol) and the mixture was stirred at RT overnight, TLC (DCM:MeOH=20:1) showed the reaction was complete. The mixture was washed with brine (8 mL×2), dried over Na$_2$SO$_4$, filtered and concentrated in vacuo and the residue was purified by chromatography (PE:EA=50:1 to 4:1) to give 6d (140 mg, 58%) as a white solid. LC-MS (Agilent): R$_t$ 3.50 min; m/z calculated for C$_{35}$H$_{32}$N$_4$O$_3$ [M+H]$^+$ 557.3. found [M+H]$^+$ 557.3.

4. Procedure for the Preparation of 6

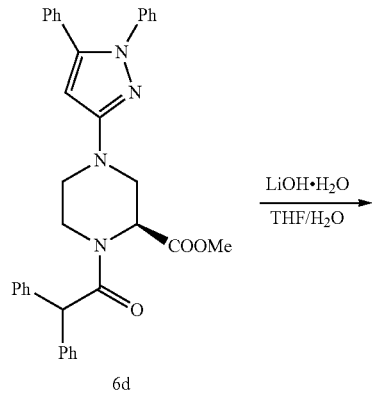

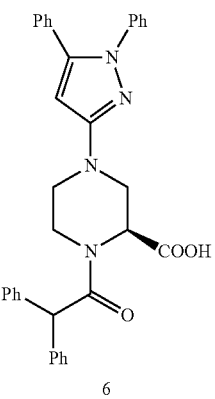

To a mixture of 6d (130 mg, 0.23 mmol) in THF (5 mL) and H$_2$O (1 mL) was added LiOH.H$_2$O (24 mg, 0.58 mmol) and the mixture was stirred at RT overnight, TLC (PE: EA=4:1) showed the starting material was consumed. Most of the THF was removed in vacuo and the residue was dissolved in water (30 mL) and washed with PE (20 mL). The aqueous layer was acidified to pH 2-3 with a 3 M aqueous HCl solution and the resulting precipitate was collected by filtration. The solid was dissolved in DCM, washed with brine, dried over Na$_2$SO$_4$, filtered and concentrated in vacuo to give 120 mg of a solid, which was re-crystallized from EA/PE to give 6 (80 mg, 64%) as a white solid. LC-MS (Agilent): R$_t$ 3.52 min; m/z calculated for C$_{34}$H$_{30}$N$_4$O$_3$ [M+H]$^+$ 543.2. found [M+H]$^+$ 543.2. HPLC (214 and 254 nm): R$_t$ 8.55 min.

Example 4: Compound 7 (3)-1-(2,2-diphenylacetyl)-4-(3-methyl-1-phenyl-1H-pyrazol-5-yl)piperazine-2-carboxylic acid 1. Procedure for the Preparation of Compound 7a

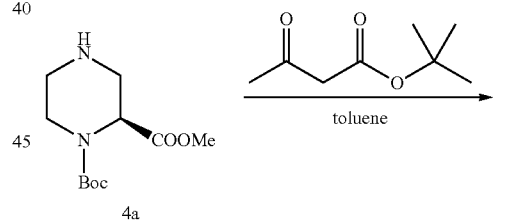

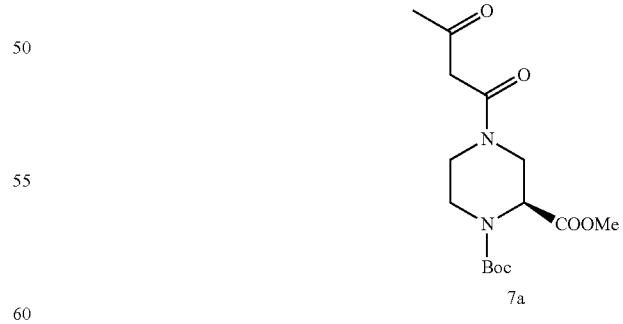

A mixture of compound 4a (600 mg, 2.5 mmol) and tert-butyl acetoacetate (427 mg, 2.7 mmol) in toluene (10 mL) was heated at 100° C. overnight, TLC (PE:EA=1:1) showed that most of the starting material was consumed. The mixture was cooled to RT, concentrated in vacuo and the residue was purified by flash chromatography (PE:EA=10:1 to 4:1) to give 7a (770 mg, 95%) as a yellow oil. LC-MS (Agilent): R$_t$ 3.19 min; m/z calculated for C$_{15}$H$_{24}$N$_2$O$_6$ [M+H]$^+$329.2, [M+Na]$^+$351.2, [M+H-t-Bu]$^+$ 272.2. found [M+H]$^+$ 329.2, [M+Na]$^+$ 351.2, [M+H-t-Bu]$^+$ 272.2.

2. Procedure for the Preparation of Compound 7b

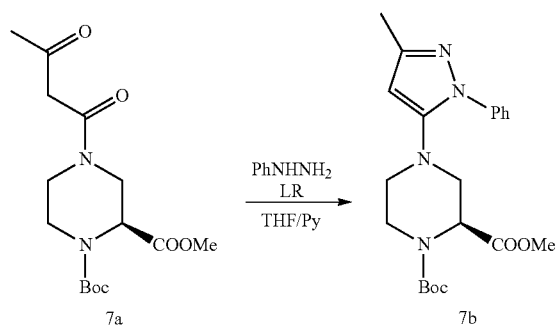 [SMILES: COC(=O)[C@@H]1CN(C(=O)CC(C)=O)CCN1C(=O)OC(C)(C)C ; "PhNHNH2LR" ; COC(=O)[C@@H]1CN(c2cc(C)nn2-c2ccccc2)CCN1C(=O)OC(C)(C)C]

A mixture of 7a (600 mg, 1.8 mmol), PhNHNH$_2$ (217 mg, 2.0 mmol) and Lawesson's reagent (808 mg, 2.0 mmol) in THF/pyridine (10 mL/1 mL) was stirred at RT for 30 min and then heated at 55° C. for 4 h, TLC (PE:EA=1:1) showed that the starting material was consumed. The reaction was cooled to RT and partitioned between EA (20 mL) and water (20 mL). The organic layer was separated, washed with a 1 M aqueous HCl solution, brine and dried over Na$_2$SO$_4$, then filtered and concentrated in vacuo. The residue was purified by chromatography (PE:EA=10:1 to 4:1) to give 7b (400 mg, 54%) as a yellow oil. LC-MS (Agilent): R$_t$ 3.47 min; m/z calculated for C$_{21}$H$_{28}$N$_4$O$_4$ [M+H]$^+$ 401.2. found [M+H]$^+$ 401.2.

3. Procedure for the Preparation of Compound 7c

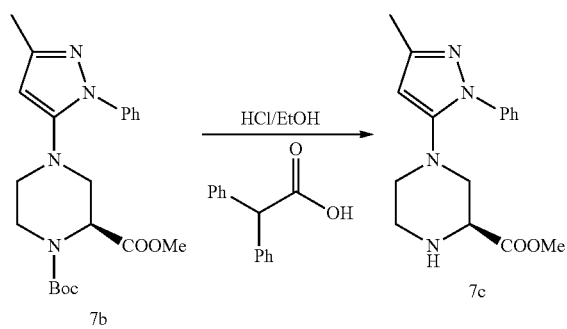

A mixture of compound 7b (400 mg, 1.0 mmol)) in a 4 M HCl/EtOH solution (10 mL) was stirred at RT for 4 h, TLC (PE:EA=1:1) showed the starting material was consumed. The mixture was concentrated in vacuo and the residue was partitioned between DCM (10 mL) and water (10 mL) and the aqueous layer was basified to pH 8-9 with a saturated aqueous NaHCO$_3$ solution. The organic layer was separated and the aqueous layer was extracted with DCM (10 mL). The combined organic extracts were washed with brine (10 mL×2), dried over Na$_2$SO$_4$, filtered and concentrated in vacuo to give the deprotected amine (250 mg) as a colorless oil, which was used in the next step without further purification. LC-MS (Waters): R$_t$ 4.16 min; m/z calculated for C$_{16}$H$_{20}$N$_4$O$_2$ [M+H]$^+$ 301.2, [M+Na]$^+$ 323.1. found [M+H]$^+$ 301.2, [M+Na]$^+$ 323.2.

4. Procedure for the Preparation of Compound 7d

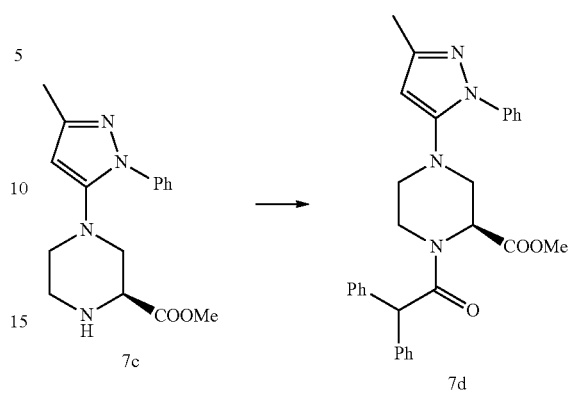

The 7c (250 mg) was dissolved in DCM (15 mL) and diphenyl acetic acid (195 mg, 0.92 mmol) was added followed by EDCI.HCl (238 mg, 0.1.24 mmol) and DMAP (cat). The mixture was then stirred at RT overnight, TLC (PE:EA=2:1) showed the reaction was complete. The mixture was diluted with DCM (15 mL) and washed with brine (20 mL). The organic layer was separated, dried over Na$_2$SO$_4$, filtered and concentrated in vacuo. The residue was purified by chromatography (PE:EA=1:0 to 10:1) to give 7d (250 mg, 50% for two steps) as a white solid. LC-MS (Agilent): R$_t$ 3.40 min; m/z calculated for C$_3$H$_{30}$N$_4$O$_3$[M+H]$^+$ 495.2, [M+Na]$^+$ 517.2. found [M+H]$^+$ 495.3, [M+Na]$^+$ 517.3.

5. Procedure for the Preparation of Compound 7

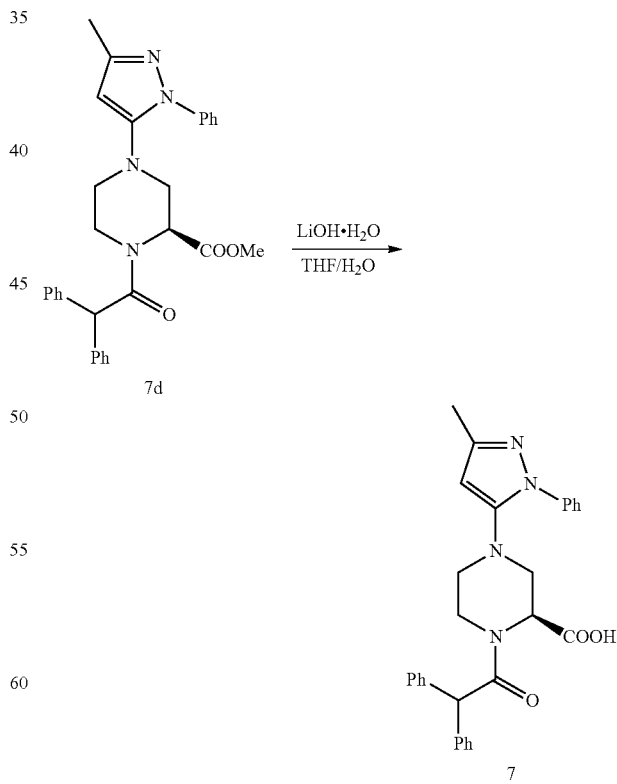

To a solution of 7d (250 mg, 0.51 mmol) in THF/H$_2$O (5 mL/1 mL) was added LiOH.H$_2$O (53 mg, 1.26 mmol) and the mixture was stirred at RT overnight, TLC (PE:EA=1:2) showed the reaction was complete. The mixture was concentrated in vacuo and the residue was dissolved in water (30 mL) and washed with Et$_2$O (20 mL). The aqueous layer was cooled in an ice-water bath and acidified to pH 4-5 with a 1 M aqueous HCl solution. The resulting white precipitate was collected by filtration, washed with water (15 mL×2) and dried at 50° C. overnight to give 7 (190 mg, 78%) as a white solid. LC-MS (Agilent): R$_t$ 3.43 min; m/z calculated for C$_{29}$H$_{28}$N$_4$O$_3$[M+H]$^+$ 481.2. found [M+H]$^+$ 481.2. HPLC (214 and 254 nm): R$_t$ 8.15 min.

Example 5: Compound 8 (S)-1-(2,2-diphenylacetyl)-4-phenethylpiperazine-2-carboxylic acid 1. Procedure for the Preparation of 8a

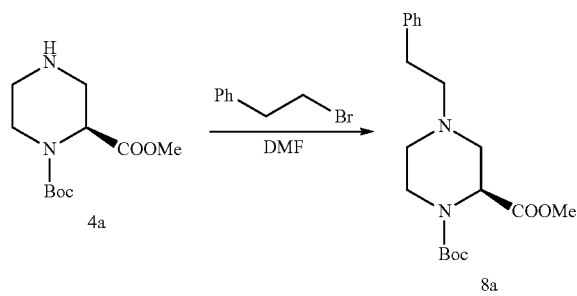

To a stirred solution of 4a (500 mg, 2.05 mmol) in DMF (10 mL) was added DIPEA (310 mg, 2.4 mmol) and 2-bromoethyl benzene (359 mg. 2.1 mmol) and the mixture was heated at 70° C. overnight, TLC (PE:EA=1:1) showed the starting material was consumed. Water (15 mL) was added and the mixture was extracted with EA (10 mL×2). The combined organic extracts were washed with brine (10 mL×2), dried over Na$_2$SO$_4$ and concentrated in vacuo to give crude 8a (1.0 g) as a colorless oil, which was used directly in the next step. LC-MS (Agilent): R$_t$ 3.32 min; m/z calculated for C$_{29}$H$_{28}$N$_2$O$_4$ [M+H]$^+$ 349.2. found [M+H]$^+$ 349.2.

2. Procedure for the Preparation of Compound 8b

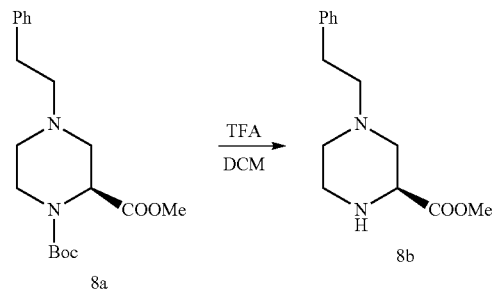

To a stirred solution of 8a (700 mg, 1.93 mmol) in DCM (10 mL) was added TFA (1.32 g, 11.58 mmol) and the mixture was stirred at RT for 5 h, TLC (PE:EA=1:1) showed the starting material was consumed. The mixture was concentrated in vacuo and the residue was diluted with water (10 mL) and washed with Et$_2$O (5 mL×2). The aqueous layer was basified to pH 9-10 with a saturated aqueous Na$_2$CO$_3$ solution and extracted with DCM (10 mL×2). The combined organic extracts were washed with brine (10 mL×2), dried over Na$_2$SO$_4$ and concentrated in vacuo to give 8b (300 mg) as a colorless oil, which was used directly in next step.

3. Procedure for the Preparation of 8c

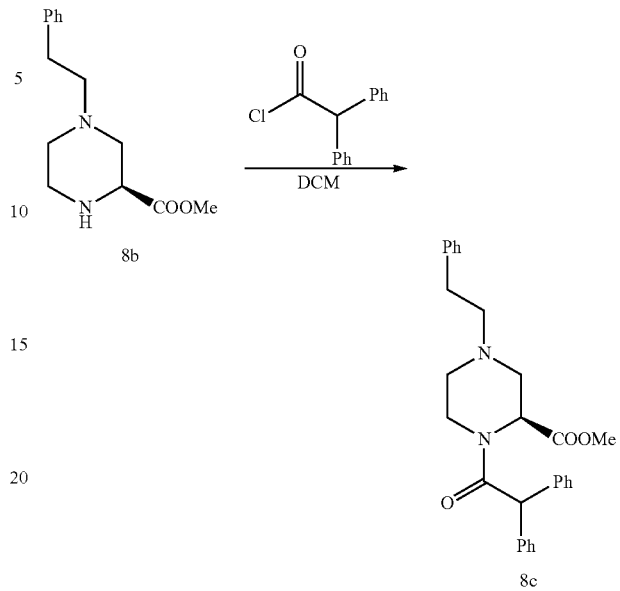

To a stirred solution of 8b (300 mg, 1.2 mmol) in DCM (5 mL) at 0° C. was added Et$_3$N (243 mg, 2.4 mmol) and diphenylacetyl chloride (331 mg, 1.44 mol) and the mixture was then stirred at RT for 1 h, TLC (DCM:MeOH=20:1) showed the starting material was consumed. DCM (5 mL) and water (5 mL) were added, the organic layer was separated, washed with brine (10 mL×2), dried over Na$_2$SO$_4$ and concentrated in vacuo. The residue was purified by chromatography (DCM:MeOH=1:0 to 20:1) to give 8c (300 mg, 62%) as a colorless oil. LC-MS (Agilent): R$_t$ 3.38 min; m/z calculated for C$_{28}$H$_{30}$N$_2$O$_3$ [M+Na]$^+$ 465.2. found [M+Na]$^+$ 465.2.

4. Procedure for the Preparation of 8

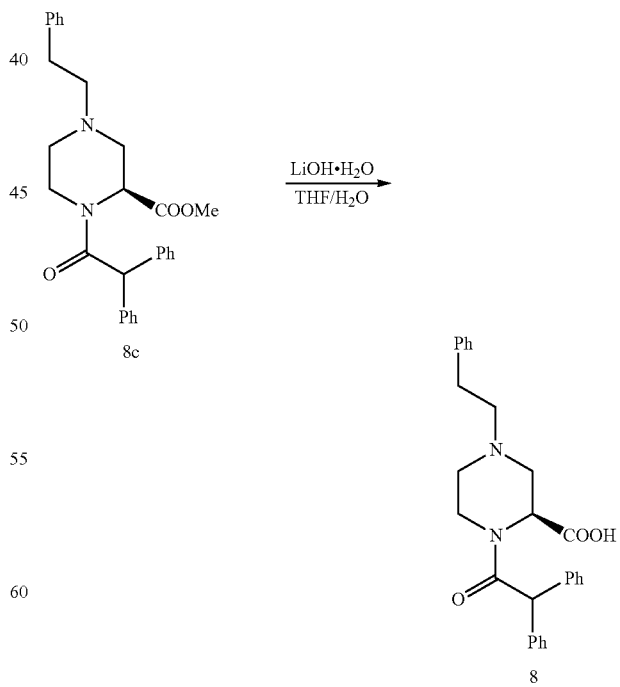

To a stirred solution of 0.8c (300 mg, 0.67 mmol) in THF (7 mL) at 0° C. was added a solution of LiOH.H$_2$O (42 mg, 1.0 mmol) in water (3 mL) and the mixture was stirred at RT overnight, TLC (PE:EA=1:1) showed the starting material was consumed. Most of the THF was removed in vacuo and the resulting aqueous solution was washed with ether (5 mL×2). EA (5 mL) was added and the aqueous layer was acidified to pH 2~3 with a 1 M aqueous HCl solution. The organic layer was collected and washed with brine, dried over $Na_2SO_4$, filtered and concentrated in vacuo to give crude 8, which was washed with hexane to give pure 8 (90 mg, 31%) as a white solid. LC-MS (Agilent): $R_t$ 3.13 min; m/z calculated for $C_{27}H_{23}N_2O_3$ $[M+H]^+$ 429.2. found $[M+H]^+$ 429.2. HPLC (214 and 254 nm): $R_t$ 11.49 min.

Example 6: Compound 9 (S)-4-cinnamyl-1-(2,2-diphenylacetyl)piperazine-2-carboxylic acid 1. Procedure for the Preparation of 9a

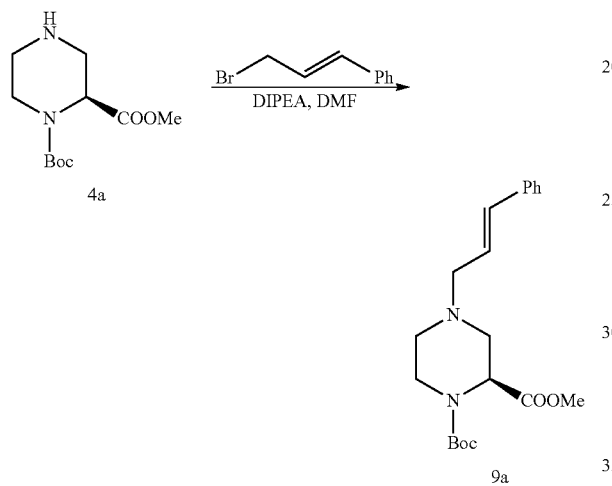

To a stirred solution of compound 4a (500 mg, 2.05 mmol) in DMF (8 mL) at 0° C. was added DIPEA (318 mg, 2.46 mmol) and trans-cinnamyl bromide (444 mg, 2.25 mmol) and the mixture was stirred at RT for 5 h, TLC (PE:EA=2:1) showed that the starting material was consumed. Water (30 mL) was added and the mixture was extracted with EA (20 mL×2). The layers were separated and the combined organic extracts were washed with water, brine and dried, over $Na_2SO_4$. The solvent was removed in vacuo to give crude 9a (0.8 g) as a yellow oil, which was used directly in the next step. LC-MS (Agilent): $R_t$ 3.11 min; m/z calculated for $C_{20}H_{28}N_2O_4$ [M+H]+361.2. found $[M+H]^+$ 361.2.

2. Procedure for the Preparation of Compound 9b

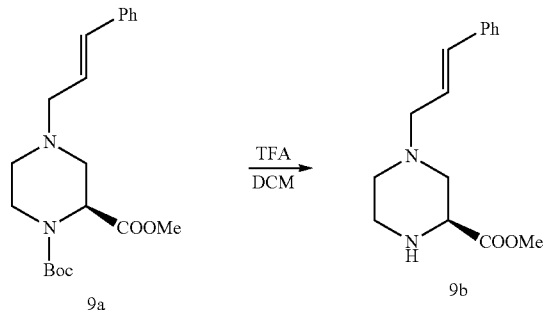 [SMILES: COC(=O)[C@@H]1CN(C/C=C/c2ccccc2)CCN1C(=O)OC(C)(C)C ; COC(=O)[C@@H]1CN(C/C=C/c2ccccc2)CCN1]

To a solution of compound 9a (0.8 g, 2.2 mmol) in DCM (10 mL) was added TFA (1.5 g, 13.3 mmol) and the mixture was stirred at RT overnight, TLC showed that the starting material was consumed. The mixture was concentrated in vacuo and the residue was dissolved in water (20 mL) and washed with $Et_2O$ (15 mL). DCM (15 mL) was added and the aqueous layer was basified to pH 7-8 with a saturated aqueous $Na_2CO_3$ solution. The organic layer was separated, washed with brine, dried over $Na_2SO_4$, filtered and concentrated in vacuo to give 9b (600 mg, 100%) as yellow oil. LC-MS (Agilent): $R_t$ 2.78 min; m/z calculated for $C_{15}H_{20}N_2O_2$ $[M+H]^+$ 261.1. found $[M+H]^+$ 261.1.

3. Procedure for the Preparation of 9c

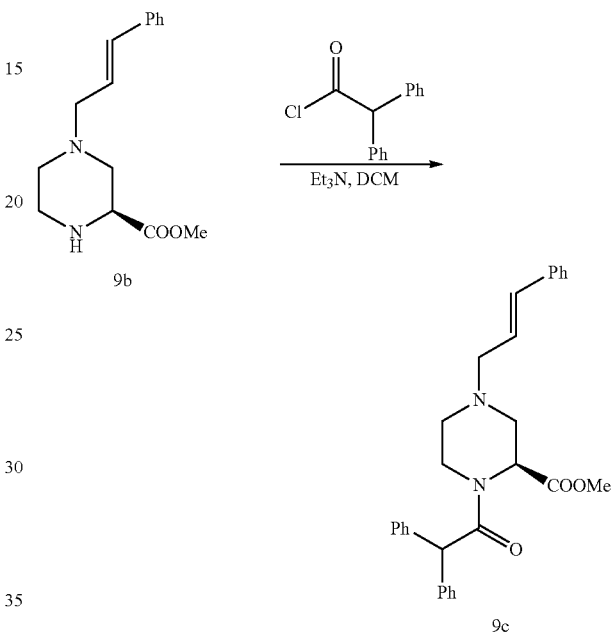

To a solution of 9b (600 mg, 2.3 mmol) in DCM (15 mL) at 0° C. was added $Et_3N$ (354 mg, 3.5 mmol) and diphenylacetyl chloride (650.0 mg, 2.8 mmol) and the mixture was stirred at RT for 10 min, TLC (PE:EA=2:1) showed that the starting material was consumed. Water (20 mL) was added, the layers were separated and the organic layer was washed with brine, dried over $Na_2SO_4$, filtered and concentrated in vacuo. Purification by silica column (PE:EA=10:1 to 4:1) gave 9c (700 mg, 70%) as a white solid. LC-MS (Agilent): $R_t$ 3.17 min; m/z calculated for $C_{29}H_{30}N_2O_3$ $[M+H]^+$ 455.2. found $[M+H]^+$ 455.2.

4. Procedure for the Preparation of 9

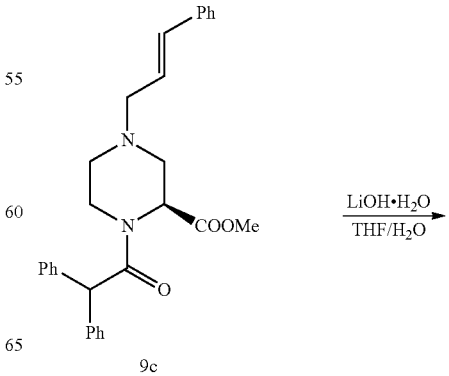

41

-continued

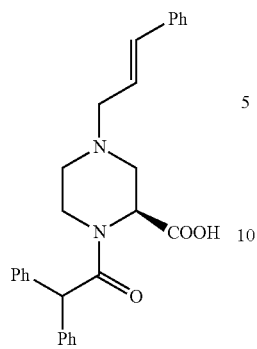

9

To a stirred mixture of 9c (700 mg, 1.5 mmol) in THF/water (10 mL/3 mL) was added LiOH.H$_2$O (194 mg, 4.5 mmol) and the mixture was stirred at RT overnight, TLC showed that the starting material was consumed. Most of the THF was removed in vacuo and the residue was dissolved in water (20 mL) and washed with Et$_2$O (15 mL). DCM (15 mL) was added and the aqueous layer was acidified to pH 2-3 with a 1 M aqueous HCl solution. The organic layer was separated and washed with brine, dried over Na$_2$SO$_4$, filtered and concentrated in vacuo. Recrystallization from EA/PE gave 9 (500 mg, 75%) as a white solid. LC-MS (Agilent): R$_t$ 3.18 min; m/z calculated for C$_{28}$H$_{28}$N$_2$O$_3$ [M+H]$^+$ 441.2. found [M+H]$^+$ 441.2. HPLC (214 and 254 nm): R$_t$ 11.87 min.

Example 7: Compound 10 (S)-1-(2,2-diphenylacetyl)-4-(3-phenylpropyl)piperazine-2-carboxylic acid

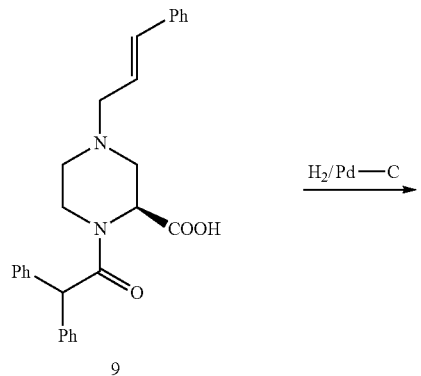

To a solution of compound 9 (300 mg, 0.68 mmol) in EA (10 mL) was added 10% Pd/C (30 mg) and the mixture was stirred at RT under a H$_2$ atmosphere (1 atm pressure) overnight, LCMS analysis showed that the starting material was consumed. The catalyst was removed by filtration through Celite and the filtrate was concentrated in vacuo. Purification by silica column (DCM:MeOH=1:0 to 20:1) gave 10 (100 mg, 33%) as a white solid. LC-MS (Agilent): R$_t$ 3.15 min; m/z calculated for C$_{28}$H$_{30}$N$_2$O$_3$ [M+H]$^+$ 443.2. found [M+H]$^+$ 443.2. HPLC (214 and 254 nm): R$_t$ 11.72 min.

Example 8: Compound 16 (S)-4-(1-benzyl-3-methyl-1H-pyrazol-5-yl)-1-(2,2-diphenylacetyl)piperazine-2-carboxylic acid 1. Procedure for the Preparation of Compound 16a

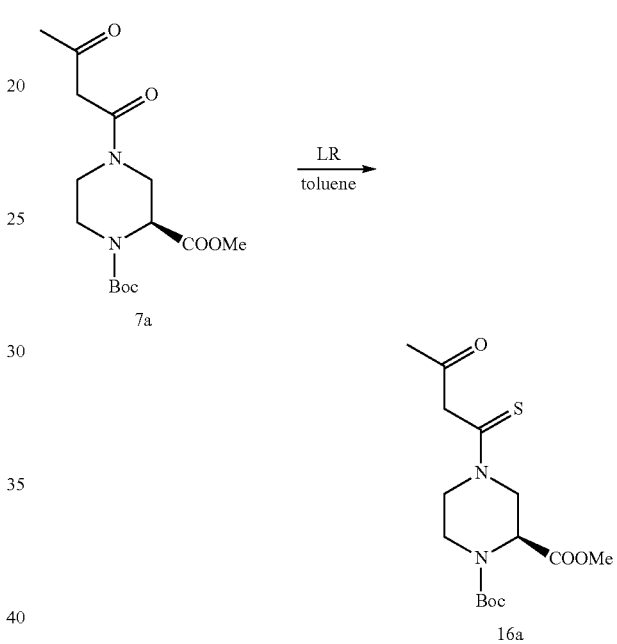

To a solution of 7a (400 mg, 1.2 mmol) in toluene (10 mL) was added Lawesson's reagent (747 mg, 0.6 mmol) and the mixture was heated at 75° C. overnight, TLC (DCM:MeOH=20:1) showed the starting material was consumed. The mixture was concentrated in vacuo and the residue was purified by silica column (PE:EA=10:1 to 4:1) to give 16a (120 mg, 29%) as a yellow oil. LC-MS (Agilent): R$_t$ 3.33 min; m/z calculated for C$_{15}$H$_{24}$N$_2$O$_5$[M+Na]$^+$ 367.1. found [M+Na]$^+$ 367.1.

2. Procedure for the Preparation of 16b

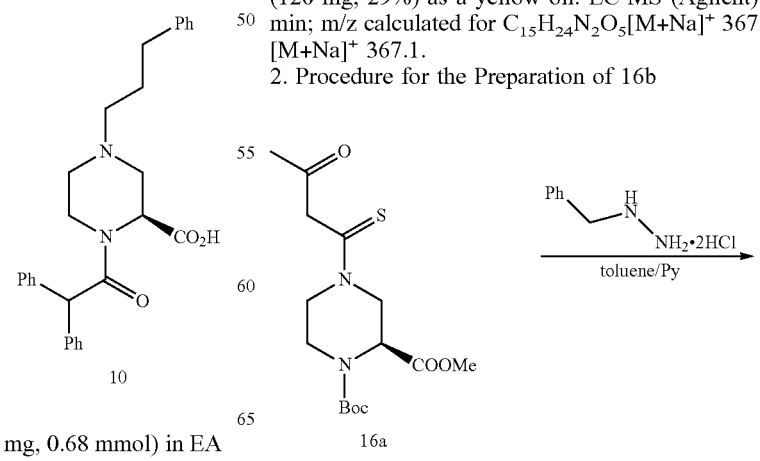

4. Procedure for the Preparation of Compound 16d

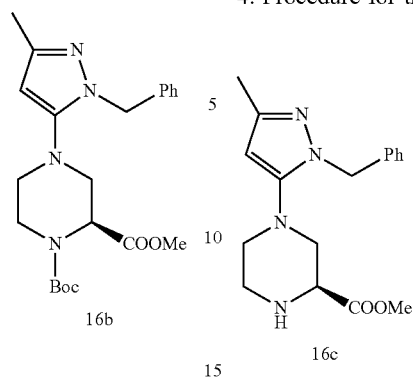

16b

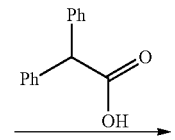

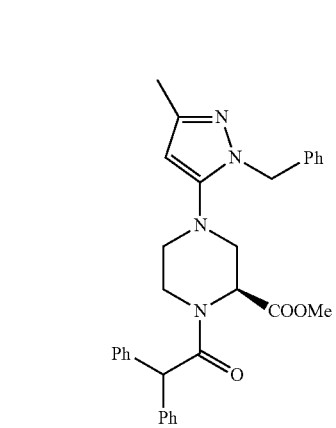

16d

To a solution of 16a (120 mg, 0.35 mmol) in toluene (10 mL) was added BnNHNH$_2$·2HCl (81.6 mg, 0.42 mmol). Two drops of pyridine were added and the mixture was heated at 90° C. overnight, TLC (PE:EA=2:1) showed the starting material was consumed. The mixture was concentrated in vacuo and the residue was purified by silica column (PE:EA=10:1 to 4:1) to give 16b (100 mg, 69%) as a yellow oil. LC-MS (Agilent): R$_t$ 3.66 min; m/z calculated for C$_{22}$H$_{30}$N$_4$O$_4$ [M+H]$^+$ 415.2, [M+Na]+437.3, [M+H]$^+$ 415.2, [M+Na]$^+$ 437.2.

3. Procedure for the Preparation of 16c

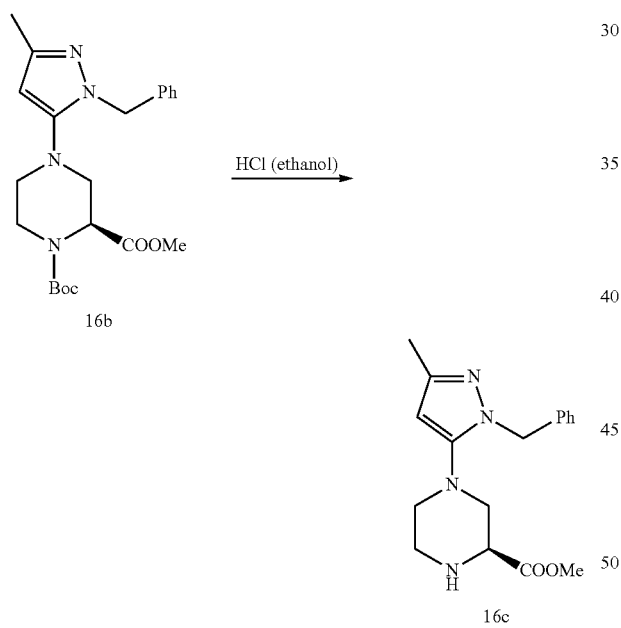

A mixture of 1613 (100 mg, 0.24 mmol) in a 4 M HCl/EtOH solution (5 mL) was stirred at RT for 3 h, TLC (PE:EA=2:1) showed that most of the starting material was consumed. Most of the ethanol was removed in vacuo and the residue was diluted with water (10 mL) and washed with Et$_2$O (10 mL). The aqueous layer was basified to pH 7-8 with a saturated aqueous Na$_2$CO$_3$ solution and extracted with DCM (10 mL×2). The combined organic extracts were washed with brine, dried over Na$_2$SO$_4$, filtered and concentrated in vacuo to give 16c (75 mg, 100%) as a yellow oil. LC-MS (Agilent): R$_t$ 3.33 min; m/z calculated for C$_{17}$H$_{22}$N$_4$O$_2$ [M+H]$^+$ 315.2, [M+Na]$^+$ 337.2, [M+H]$^+$ 315.2, [M+Na]$^+$ 337.1.

To a solution of 16c (70.0 mg, 0.22 mmol) and diphenyl acetic acid (52.0 mg, 0.25 mmol) in DCM (5 mL) was added EDCI.HCl (85.5 mg, 0.44 mmol) and DMAP (5 mol %) and the mixture was stirred at RT overnight, TLC (PE:EA=2:1) showed that the starting material was consumed. The mixture was diluted with DCM and washed with saturated NaHCO$_3$ solution, brine, dried over Na$_2$SO$_4$ and concentrated in vacuo. Purification, by silica column (PE:EA=10:1 to 5:1) gave 16d (95 mg, 86%) as a yellow solid. LC-MS (Agilent): 3.53 min; m/z calculated for C$_{31}$H$_{32}$N$_4$O$_3$ [M+H]$^+$ 509.2, [M+Na]$^+$ 531.3, [M+H]$^+$ 509.2, [M+Na]$^+$ 531.2.

5. Procedure for the Preparation of 16

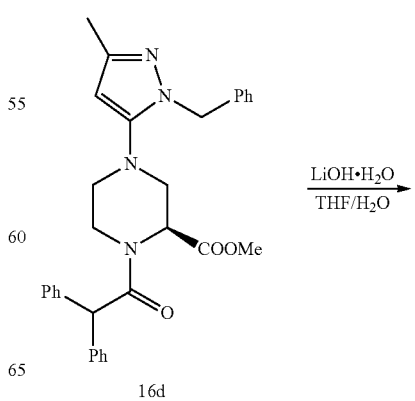

16d

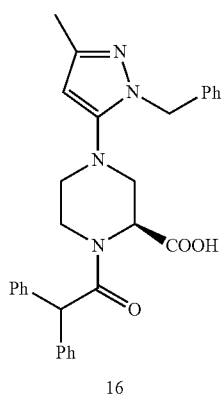

16

To a mixture of 16d (90.0 mg, 0.18 mmol) in THF/water (6 mL/2 mL) was added LiOH.H$_2$O (22.3 mg, 0.53 mmol) and the mixture was stirred at RT overnight; TLC showed that the starting material was consumed. Most of the THF was removed in vacuo and the residue was dissolved in water (20 mL) and washed with Et$_2$O (15 mL). The aqueous layer was acidified to pH 3 with a 1 M aqueous HCl solution and the resulting precipitate was collected by filtration and dried to give 16 (55 mg, 63%) as a white solid. LC-MS (Agilent): R$_t$ 3.48 min; m/z calculated for C$_{30}$H$_{30}$N$_4$O$_3$ [M+H]$^+$ 495.2. found [M+H]$^+$ 495.2. HPLC (JULY-L) (214 and 254 nm): R$_t$ 8.21 min.

Example 9: Compound 17 (S)-4-(1-benzyl-5-methyl-1H-pyrazol-3-yl)-1-(2,2-diphenylacetyl)piperidine-2-carboxylic acid 1. Procedure for the Preparation of 17a

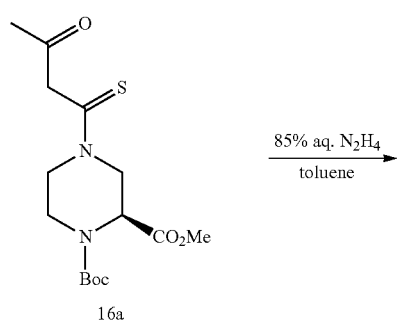

16a

To a solution of 16a (450 mg, 1.3 mmol) in toluene (10 mL) was added N$_2$HNH$_2$.H$_2$O (85% solution in water, 197 mg, 3.4 mmol) and the mixture was heated at 70° C. overnight, TLC (DCM:MeOH=20:1) showed that the starting material was consumed. The mixture was concentrated in vacuo and the residue was purified by column chromatography (DCM:MeOH=100:1 to 50:1) to give 17a (350 mg, 83%) as a yellows solid. LC-MS (Agilent): R$_t$ 3.64 min; m/z calculated for C$_{15}$H$_{24}$N$_4$O$_4$[M+H]$^+$ 325.2. found [M+H]$^+$ 325.2.

2. Procedure for the Preparation of 17b

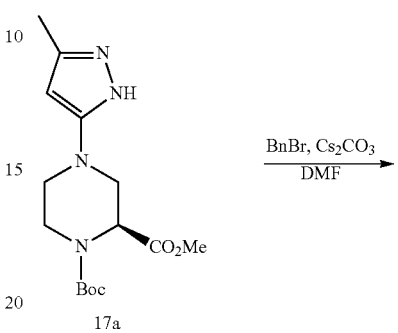

17a

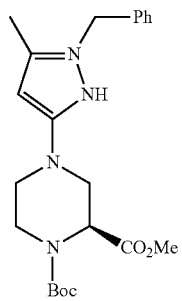

+ 1-benzyl-3-methyl isomer

17b

A mixture of 17a (320 mg, 0.99 mmol), benzyl bromide (186 mg, 1.09 mmol) and Cs$_2$CO$_3$ (387 mg, 1.2 mmol) in DMF (8 mL) was heated at 45° C. overnight, TLC (DCM:MeOH=20:1) showed that most of the starting material was consumed. The mixture was cooled to RT, poured into ice-water (30 mL) and extracted with EA (20 mL×2). The combined organic extracts were washed with brine, dried over Na$_2$SO$_4$, filtered and concentrated in vacuo. Purification by column chromatography (DCM:MeOH=1:0 to 20:1) gave 17b (300 mg, 73%) as a yellow oil and recovered starting material (60 mg, 19%). LC-MS (Agilent): R$_t$ 3.93 min; m/z calculated for C$_{22}$H$_{30}$N$_4$O$_4$ [M+H]$^+$ 415.2. found, [M+H]$^+$ 415.2.

3. Procedure for the Preparation of 17c

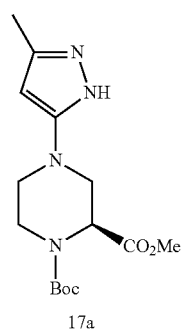

17a

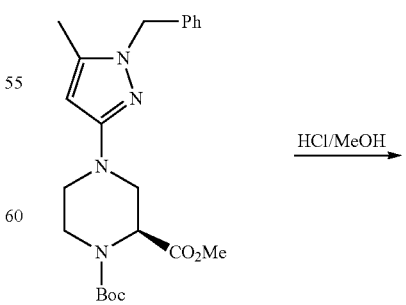

+ 1-benzyl-3-methyl isomer

17b

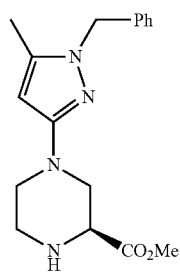

+ 1-benzyl-3-methyl isomer

17c

A mixture of 17b (300 mg, 0.72 mmol) in a 4 M HCl/MeOH solution was stirred at RT for 3 h, TLC showed that the starting material was consumed. The mixture was concentrated in vacuo and the residue was partitioned between DCM (20 mL) and a saturated aqueous NaHCO$_3$ solution (30 mL). The layers were separated and the aqueous layer was further extracted with DCM (20 mL). The combined organic extracts were washed with brine, dried over Na$_2$SO$_4$, filtered and concentrated in vacuo to give crude 17c (240 mg, >100%) as a yellow oil, which was used directly in the next step. LC-MS (Agilent): R$_t$ 3.32 min; mh calculated for C$_{17}$H$_{22}$N$_4$O$_2$ [M+H]$^+$ 315.2, [M+Na]$^+$ 337.2. found, [M+H]$^+$ 315.2, [M+Na]$^+$ 337.2.

4. Procedure for the Preparation of 17d

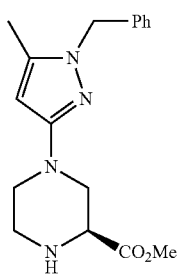 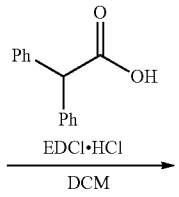

17c
+ 1-benzyl-3-methyl isomer

EDCl·HCl
DCM
→

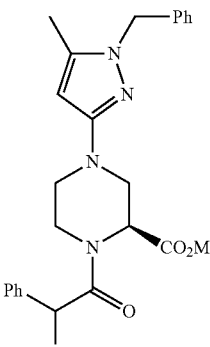

17d
+ 1-benzyl-3-methyl isomer

To a solution of 17c (240 mg, 0.76 mmol) and diphenyl acetic acid (195 mg, 0.92 mmol) in DCM (10 mL) was added EDCI.HCl (190 mg, 0.99 mmol) and the mixture was stirred at RT overnight, TLC (DCM:MeOH=10:1) showed that the starting material was consumed. The mixture was washed with brine (10 mL), dried over Na$_2$SO$_4$, filtered and concentrated in vacuo. The residue was purified by column chromatography (DCM:MeOH=1:0 to 20:1) to give 17d (320 mg, 82%) as thick colorless oil. LC-MS (Agilent): R$_t$ 3.98 min; ink calculated for C$_{31}$H$_{32}$N$_4$O$_3$[M+H]$^+$ 509.3, [M+Na]$^+$ 531.3, [M+H]$^+$ 509.3, [M+Na]$^+$ 531.2.

5. Procedure for the Preparation of 17

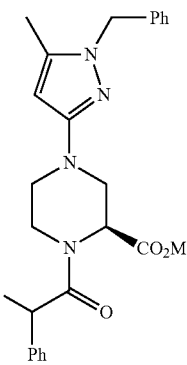

LiOH·H$_2$O
→

17d
+ 1-benzyl-3-methyl isomer

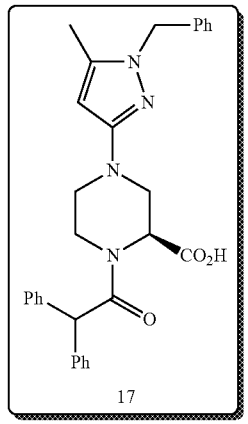

17
+ 1-benzyl-3-methyl isomer

To a mixture of 0.17d (160 mg, 0.31 mmol) in THF/water (10 mL/1.5 mL) was added LiOH.H$_2$O (40 mg, 0.94 mmol) and the mixture was stirred at RT overnight, LCMS analysis showed that the starting material was consumed. Most of the THF was removed in vacuo and the residue was dissolved in water (10 mL), acidified to pH 4-5 with a 3 M aqueous HCl solution and extracted with DCM (15 mL×2). The combined organic extracts were washed with brine, dried over Na$_2$SO$_4$, filtered and concentrated in vacuo to give 17 and 16 in a 4:1 ratio (150 mg, 98%) as a white solid. Ratio determined by integration of the $^1$H NMR spectrum. LC-MS (Agilent): R$_t$ 4.01 min; m/z calculated for C$_{30}$H$_{30}$N$_4$O$_3$ [M+H]$^+$ 495.2. found [M+H]$^+$ 495.3. HPLC (214 and 254 nm): R$_t$ 9.21 min.

Example 10: Compound 23 (S)-4-(1-benzyl-3-(-trifluoromethyl)-1H-pyrazol-5-yl)-1-(2,2-diphenylacetyl)piperazine-2-carboxylic acid 1. Procedure for the Preparation of 23a

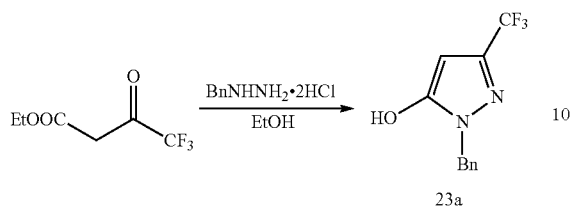

A mixture of ethyl 4,4,4-trifluoro-3-oxobutanoate (4.72 g, 25.6 mmol), benzyl-hydrazine dihydrochloride (5.00 g, 25.63 mmol) and TsOH·H$_2$O (490 mg, 2.56 mmol) in EtOH (30 mL) was heated at reflux overnight, TLC (PE:EA=2:1) showed that the starting material was consumed. The mixture was concentrated in vacuo and the residue was partitioned between EA (15 mL) and water (15 mL). The organic layer was separated, washed with brine (10 mL×2), dried over Na$_2$SO$_4$, filtered and concentrated in vacuo. The residue was re-crystallised from Et$_2$O to give 23a (2.22 g, 36%) as a white solid. LC-MS (Agilent): R$_t$ 3.75 min; m/z calculated for C$_{11}$H$_9$F$_3$N$_2$O [M+H]$^+$ 243.1, [M+Na]$^+$ 265.1. found [M+H]$^+$ 243.1, [M+Na]$^+$ 265.1.

2. Procedure for the Preparation of 23b

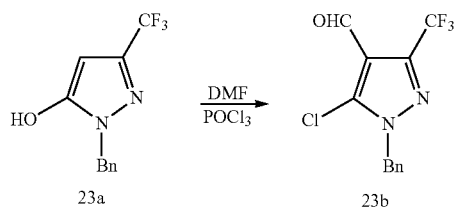

To a mixture of 23a (222 g, 9.17 mmol) and DMF (2.68 g, 36.7 mol) was added POCl$_3$ (10 mL) dropwise at 0° C. The mixture was then heated at 80° C. under a N$_2$ atmosphere for 5 h, TLC (PE:EA=2:1) showed that the starting material was consumed. The mixture was allowed to cool to RT, poured into ice-water (150 mL) and extracted with EA (50 mL). To the organic layer was added water (40 mL) and the aqueous layer was adjusted to pH 7 with K$_2$CO$_3$. The organic layer was collected, washed with brine (40 mL), dried over Na$_2$SO$_4$, filtered and concentrated in vacuo. The residue was purified by chromatography (PE:EA=1:0 to 10:1) to give 23b (1.78 g, 67%) as a thick yellow oil. LC-MS (Agilent): R$_t$ 4.08 min; m/z calculated for C$_{12}$H$_8$ClF$_3$N$_2$O [M+H]$^+$ 289.0. [M+Na]$^+$ 311.0. found [M+H]$^+$ 289.0. [M+Na]$^+$ 311.0.

3. Procedure for the Preparation of 23c

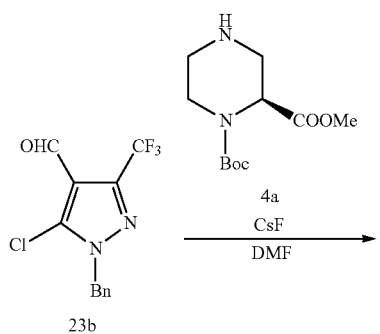

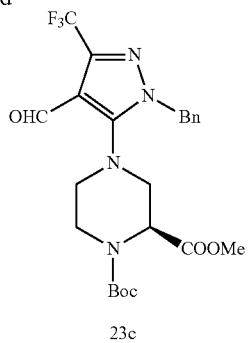

A mixture of 23b (1.78 g, 6.16 mmol), 4a (1.81 g, 7.40 mmol) and CsF (6.55 g, 43.2 mmol) in DMF (30 mL) was heated at 80° C. under a N$_2$ atmosphere overnight, TLC (PE:EA=10:1) showed that the starting material was consumed. The mixture was allowed to cool to RT, poured into ice water (250 mL) and extracted with EA (80 mL×2). The combined organic extracts were washed with brine (100 mL), dried over Na$_2$SO$_4$, filtered and concentrated in vacuo. The residue was purified by chromatography (PE:EA=25:1 to 10:1) to give 23c (1.29 g, 42%) as a red solid. LC-MS (Agilent): R$_t$ 4.43 min; m/z calculated for C$_{23}$H$_{27}$F$_3$N$_4$O$_5$ [M-Boc+H]$^+$ 397.1. [M+Na]$^+$ 519.2. found [M-Boc+H]$^+$ 397.1. [M+Na]$^+$ 519.2.

4. Procedure for the Preparation of 23d

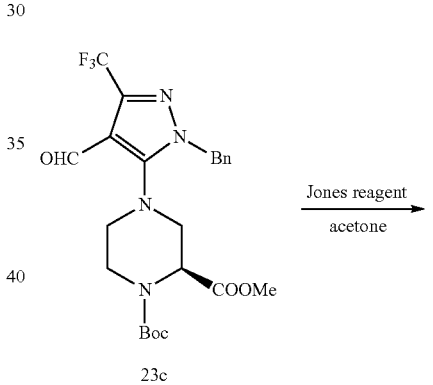

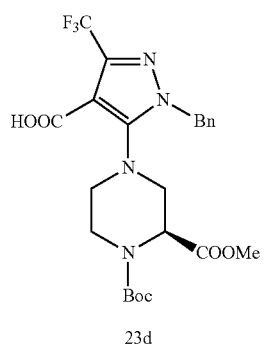

To a solution of 23c (1.29 g, 2.60 mmol) in acetone (30 mL) at 0° C. was added Jones reagent (7.0 ml 5.2 mmol) dropwise and the mixture was stirred at 0° C. for 2 h, TLC (PE:EA=4:1) showed that most of the starting material was consumed. The reaction was quenched with isopropanol (3 mL), stirred for 5 min then filtered to remove the precipitate and the filtrate was concentrated in vacuo. The residue was dissolved in water (20 mL), basified to pH 8 with Et$_3$N and extracted with DCM (15 mL×2). The combined organic extracts were washed with brine (30 mL×2), dried over Na$_2$SO$_4$, filtered and concentrated in vacuo. The residue was purified by chromatography (PE:EA=10:1 to 4:1) to give 23d (450 mg, 34%) as a white solid. LC-MS (Agilent): R$_t$ 4.25 min; m/z calculated for C$_{23}$H$_{27}$F$_3$N$_4$O$_6$ [M-Boc+H]$^+$ 413.1, [M+H]$^+$ 513.2, [M+Na]$^+$ 535.2. found [M-Boc+H]$^+$ 413.1, [M+H]$^+$ 513.2, [M+Na]$^+$ 535.2.

5. Procedure for the Preparation of 23e

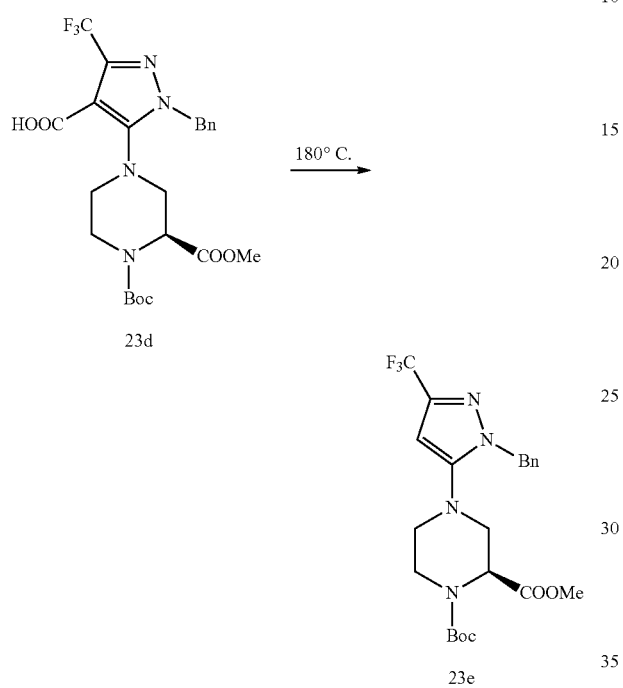

23d (380 mg, 0.74 mmol) was heated at 180° C. under a N$_2$ atmosphere for 2 h, TLC (PE:EA=2:1) showed that the starting material was consumed, then cooled to RT to give 23e (300 mg) as grey oil, which was used directly in the next step. LC-MS (Agilent): R$_t$ 3.96 min; m/z calculated for C$_{22}$H$_{27}$F$_3$N$_4$O$_4$ [M+H]$^+$ 469.2, [M+Na]$^+$ 491.2. found [M+H]$^+$ 469.2, [M+Na]$^+$ 491.2.

6. Procedure for the Preparation of 23f

To a solution of 23e (300 mg) in MeOH (5 mL) was added a 4 M HCl/MeOH solution (25 mL) and the mixture was stirred at RT overnight, TLC (DCM:MeOH=10:1) showed that the starting material was consumed. The mixture was concentrated in vacuo and the residue was dissolved in water (20 mL) and washed with Et$_2$O. The aqueous phase was basified to pH 7-8 with K$_2$CO$_3$ and extracted with EA (15 mL×2). The combined organic extracts were dried over Na$_2$SO$_4$, filtered and concentrated in vacuo. The residue was purified by chromatography (PE:EA=7:1 to 1:1) to give 23f (100 mg, 42%) as a colorless oil. LC-MS (Agilent): R$_t$ 3.76 min; m/z calculated for C$_{17}$H$_{19}$F$_3$N$_4$O$_2$ [M+H]$^+$ 369.2, [M+Na]$^+$ 391.2. found [M+H]$^+$ 369.2, [M+Na]$^+$ 391.2.

7. Procedure for the Preparation of 23f

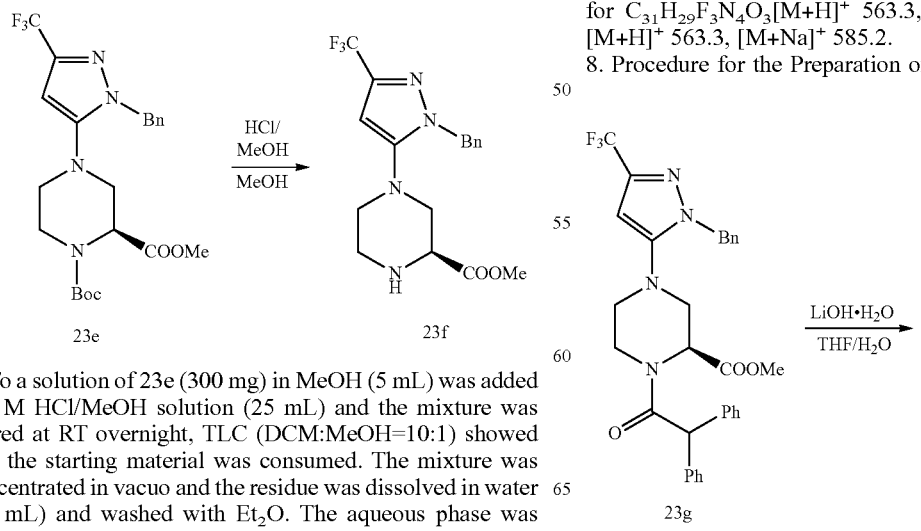

To solution of 23f (90 mg, 0.24 mmol) and Et$_3$N (32 mg, 0.32 mmol) in DCM (20 mL) at 0° C. was added diphenylacetyl chloride (68 mg, 0.29 mmol) and the mixture was stirred at RT overnight, TLC (PE:EA=4:1) showed that a major new product was formed. The mixture was washed with brine (15 mL×2), dried over Na$_2$SO$_4$, filtered and concentrated in vacuo. The residue was purified by chromatography (PE:EA=10:1 to 5:1) to give 23g (100 mg, 73%) as a white solid. LC-MS (Agilent): R$_t$ 4.01 min; m/z calculated for C$_{31}$H$_{29}$F$_3$N$_4$O$_3$[M+H]$^+$ 563.3, [M+Na]$^+$ 585.2. found [M+H]$^+$ 563.3, [M+Na]$^+$ 585.2.

8. Procedure for the Preparation of 23

-continued

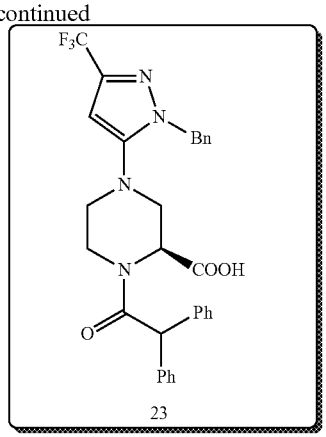

23

A mixture of 23g (100 mg, 0.18 mmol) and LiOH·H$_2$O (23 mg, 0.53 mmol) in THF/water (8 mL/2 mL) was stirred at RT overnight, TLC (DCM:MeOH=10:1) showed the starting material was consumed. Most of the THF was removed in vacuo and the residue was dissolved in water (10 mL) and acidified to pH 4~5 with a 3 M aqueous HCl solution. The resulting precipitate was collected by filtration and dried at 60° C. to give 23 (78 mg, 80%) as a white solid. LC-MS (Agilent): R$_t$ 4.51 min; m/z calculated for C$_{30}$H$_{27}$N$_4$O$_3$ [M+H]$^+$ 549.2, [M+Na]$^+$ 571.2. found [M+H]$^+$ 499.2, [M+Na]$^+$ 571.2. HPLC (JULY-L) (214 and 254 nm)): R$_t$ 9.27 min.

Example 11: Compound 24 (S)-1-(2,2-diphenylacetyl)-4-(3-phenylprop-2-yn-1-yl)piperazine-2-carboxylic acid 1. Procedure for the Preparation of 24b

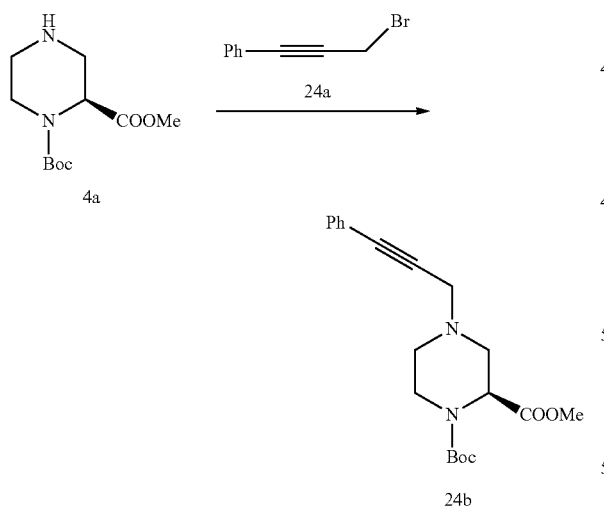

To a solution of 4a (150 mg, 0.61 mmol) in DMF (5 mL) was added K$_2$CO$_3$ (102 mg, 0.74 mmol) and 24a (144 mg, 0.74 mmol) and the mixture was heated at 70° C. overnight, TLC (DCM:MeOH=10:1) showed that the starting material was consumed. The mixture was poured into ice-water (20 mL) and extracted with EA (15 mL×2). The combined organic extracts were washed with brine (20 mL), dried over Na$_2$SO$_4$, filtered and concentrated in vacuo. The residue was purified by chromatography (PE:EA=10:1 to 8:1) to give 24b (70 mg, 31%) as a colorless oil. LC-MS (Agilent, P-2): R$_t$ 3.19 min; m/z calculated for C$_{20}$H$_{26}$N$_2$O$_4$ [M+H]$^+$ 359.2, [M+Na]$^+$ 381.2. found [M+H]$^+$ 359.2, [M+Na]$^+$ 381.2.

2. Procedure for the Preparation of 24c

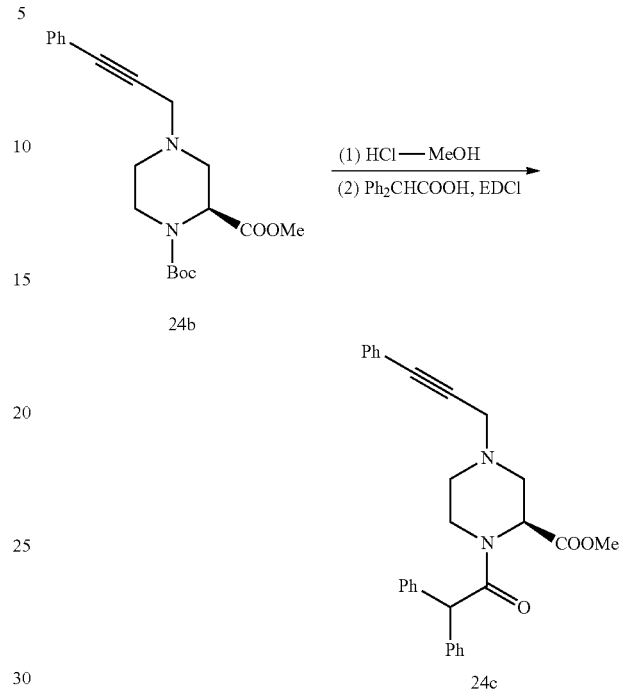

A mixture of 24b (70 mg, 0.20 mmol) and a 4 M HCl/MeOH solution (5 mL) was stirred at RT overnight, TLC (PE:EA=2:1) showed that the starting material was consumed. The mixture was concentrated in vacuo, the residue was dissolved in water (10 mL), basified to pH 9 with K$_2$CO$_3$ and extracted with DCM (10 mL×2). The combined organic extracts were dried over Na$_2$SO$_4$, filtered and concentrated in vacuo. The residue was dissolved in DCM (5 mL), diphenyl acetic acid (45 mg, 0.22 mmol) and EDCI (45 mg, 0.23 mmol) were added and the mixture was stirred at RT overnight, TLC (DCM:MeOH=10:1) showed that the starting material was consumed. The mixture was washed with water (5 mL), brine (5 mL×2), dried over Na$_2$SO$_4$, filtered and concentrated in vacuo. The residue was purified by chromatography (PE:EA=10:1 to 4:1) to give 24c (37 mg, 42%) as a colorless oil. LC-MS (Agilent, P-2): R$_t$ 3.10 min; m/z calculated for C$_{29}$H$_{28}$N$_2$O$_3$ [M+H]$^+$ 453.2. found [M+H]$^+$ 453.2.

3. Procedure for the Preparation of 24

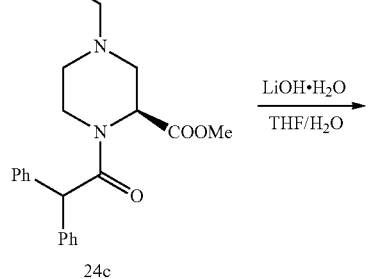

24c

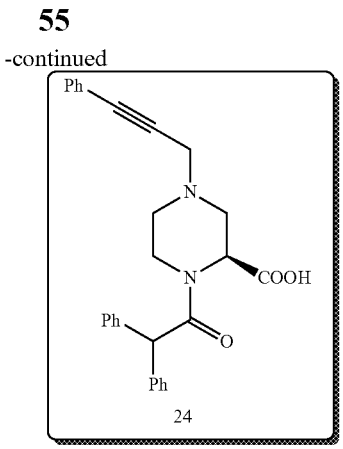

A mixture of 24c (37 mg, 0.081 mmol) and LiOH.H₂O (10 mg, 0.245 mmol) in THF/H₂O (2 mL/0.5 mL) was stirred at RT overnight, TLC (PE:EA=2:1) showed the starting material was consumed. The mixture was concentrated in vacuo, the residue was dissolved in water (2 mL), acidified to pH 4~5 with a 4 M aqueous HCl solution and extracted with DCM (5 mL×2). The combined organic extracts were washed with brine (5 mL), dried over Na₂SO₄, filtered and concentrated in vacuo. The residue was purified by preparative HPLC to give 24 (15 mg, 41%) as a white solid. LC-MS (Agilent, P-2); $R_t$ 3.10 min; m/z calculated for $C_{28}H_{26}N_2O_3[M+H]^+$ 439.2. found $[M+H]^+$ 439.2. HPLC (JULY-L) (214 and 254 nm): $R_t$ 9.04 min.

Example 12: Compound 25 (S)-1-(2,2-diphenylacetyl)-4-(3-fluorophenylprop-2-yn-1-yl)piperazine-2-carboxylic acid 1. Procedure for the Preparation of 25a

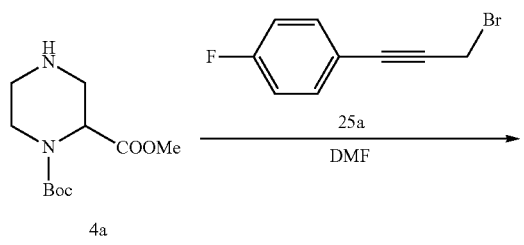

To a solution of 4a (200 mg, 0.82 mmol) in DMF (5 mL) was added K₂CO₃ (170 mg, 1.23 mmol) and 25a (170 mg, 0.81 mmol) and the mixture was stirred at 30° C. overnight, TLC (PE:EA=2:1) showed that the starting material was consumed. The mixture was partitioned between EA (20, mL) and H₂O (20 mL), the organic layer was separated, washed with brine, dried over Na₂SO₄, filtered and concentrated in vacuo. The residue was purified by chromatography (PE:EA=10:1 to 2:1) to give 25b (100 mg, 32%) as a brown oil. LC-MS (Agilent, P-2): $R_t$ 3.277 min; m/z calculated for $C_{20}H_{25}FN_2O_4$ $[M+H]^+$ 377.2, $[M+Na]^+$ 399.2. found $[M+H]^+$ 377.2, $[M+Na]^+$ 399.2.

2. Procedure for the Preparation of 25c

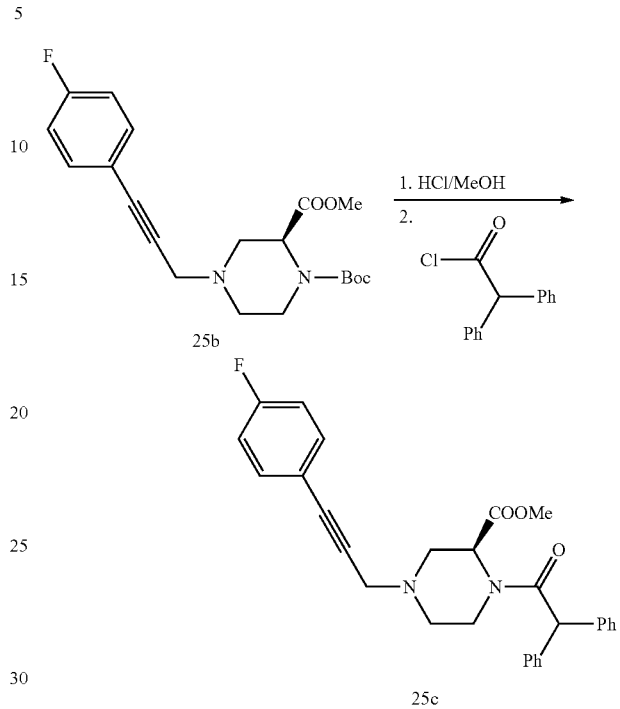

A mixture of 25b (100 mg, 0.27 mmol) and a 4 M HCl/MeOH solution (5 mL) was stirred at RT overnight, TLC (PE:EA=2:1) showed that the starting material was consumed. The mixture was concentrated in vacuo, the residue was dissolved in water, basified to pH 9-10 with K₂CO₃ and extracted with DCM (20 mL×3). The combined organic extracts were dried over Na₂SO₄, filtered and concentrated. The residue was dissolved in DCM (5 mL), TEA (42 mg, 0.41 mmol) and 2,2-diphenylacetyl chloride (74 mg, 0.32 mmol) were added at 0° C. and the mixture was allowed to warm to RT and stirred for 10 min, TLC (DCM: MeOH=10:1) showed that the starting material was consumed. The reaction was quenched with water and the organic layer was separated, washed with brine, dried over Na₂SO₄, filtered and concentrated in vacuo. The residue was purified by chromatography (PE:EA=10:1 to 1:1) to give 25c (100 mg, 77%) as a yellow oil. LC-MS (Agilent, P-2): $R_t$ 3.449 min; m/z calculated for $C_{29}H_{27}FN_2O_3[M+H]^+$ 471.2. found $[M+H]^+$ 471.2.

3. Procedure for the Preparation of 25

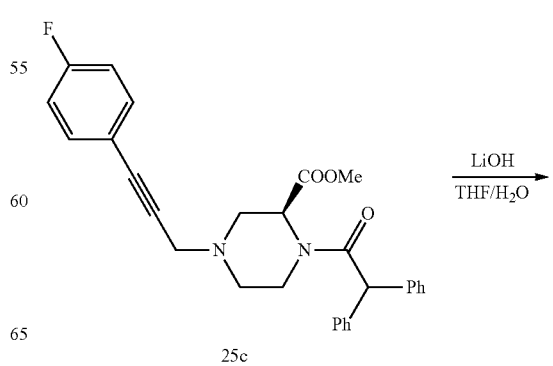

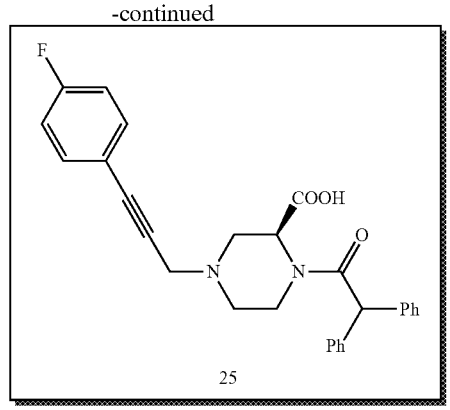

A mixture of 25c (100 mg, 0.21 mmol) and LiOH.H₂O (36 mg, 0.85 mmol) in THF/H₂O (3 mL/1 mL) was stirred at RT overnight, TLC (PE:EA=1:2) showed that the starting material was consumed. The mixture was concentrated in vacuo, the residue was dissolved in water (5 mL) and acidified to pH 3~4 with a 3 M aqueous HCl solution. The resulting precipitate was collected by filtration and dried to give 25 (66 mg, 69%) as a white solid. LC-MS (Agilent, P-2): $R_t$ 3.206 min; m/z calculated for $C_{28}H_{25}FN_2O_3$ [M+H]⁺ 457.2. found [M+H]⁺ 457.2. HPLC (JULY-L) (214 and 254 nm): $R_t$ 9.071 min.

Example 13: Compound 26 (S)-1-(2,2-diphenylacetyl)-4-(4-phenylbut-3-yn-1-yl)piperazine-2-carboxylic acid 1. Procedure for the Preparation of 26a

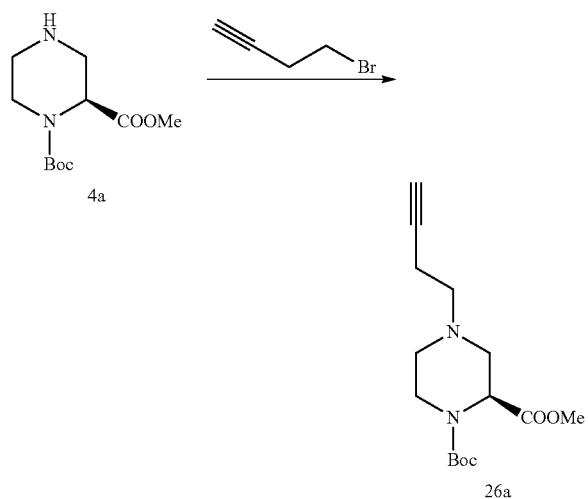

A mixture of 4a (500 mg, 2.05 mmol), K₂CO₃ (339 mg, 2.46 mmol) and 4-bromo-1-butyne (273 mg, 2.05 mmol) in DMF (5 mL) was heated at 60° C. overnight. More 4-bromo-1-butyne (273 mg, 2.05 mmol) was added and heating was continued at 60° C. for 6 h, TLC (DCM:MeOH=10:1) showed the starting material was consumed. The mixture was poured into ice-water (30 mL) and extracted with EA (10 mL×2), the combined organic extracts were washed with brine (10 mL), dried over Na₂SO₄, filtered and concentrated in vacuo. The residue was purified by chromatography (PE:EA=1:0 to 9:1) to give 26a (367 mg, 60%) as a colorless oil. LC-MS (Agilent, P-2): $R_t$ 2.85 min; m/z calculated for $C_{15}H_{24}N_2O_4$ [M+H]⁺ 296.2, [M+Na]⁺ 319.2. found [M+H]⁺ 296.2, [M+Na]⁺ 319.2.

2. Procedure for the Preparation of 26b

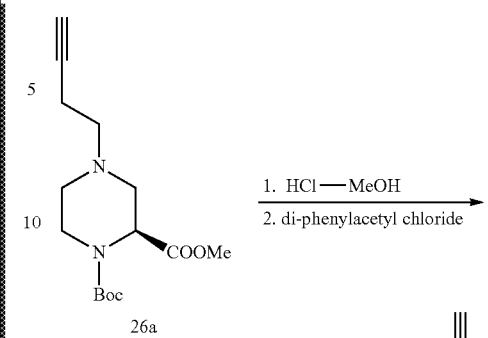

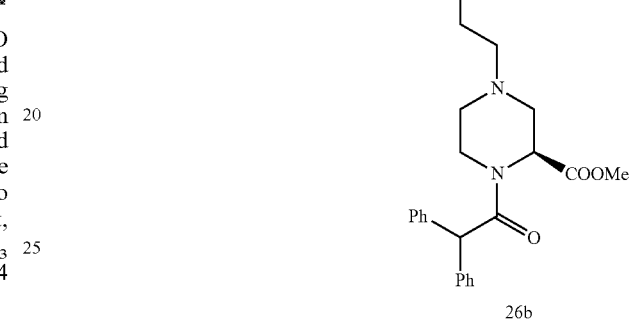

A mixture of 26a (367 mg, 1.24 mmol) in 4 M HCl/MeOH (10 mL) was stirred at RT overnight, TLC (PE:EA=4:1) showed that the starting material was consumed. The mixture was concentrated in vacuo, the residue was dissolved in water (10 mL), basified to pH 9~10 with K₂CO₃ and extracted with IPA/CHCl₃ (1/3 v/v, 8 mL×7). The combined organic extracts were dried over Na₂SO₄, filtered and concentrated in vacuo. The residue was dissolved in DCM (10 mL) and cooled to 0° C. Et₃N (205 mg, 1.49 mmol) was added followed by the slow addition of diphenyl acetyl chloride (343 mg, 1.49 mmol). The mixture was stirred at RT for 10 min, TLC (DCM:MeOH=10:1) showed that the starting material was consumed. The mixture was washed with water (10 mL), brine (10 mL), dried over Na₂SO₄, filtered and concentrated in vacuo. The residue was purified by chromatography (PE:EA=10:1 to 5.5:1) to give 26b (331 mg, 68%) as colorless oil. LC-MS (Agilent, P-2): $R_t$ 3.07 min; m/z calculated for $C_{24}H_{26}N_2O_3$ [M+H]⁺ 391.2, [M+Na]⁺ 413.2. found [M+H]⁺ 391.2, [M+Na]⁺ 413.2.

3. Procedure for the Preparation of 26c

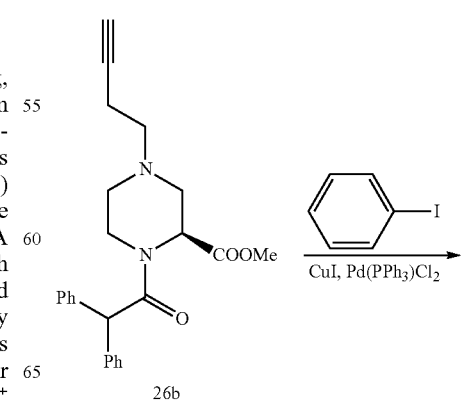

-continued

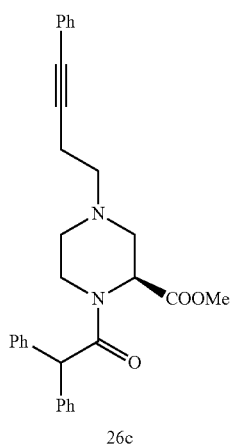

26c

A mixture of 26b (50 mg, 0.13 mmol), iodobenzene (31 mg, 0.15 mmol), CuI (2 mg, 0.006 mmol), Pd(PPh$_3$)Cl$_2$ (9 mg, 0.013 mmol) and Et$_3$N (39 mg, 0.39 mmol) in THF (5 mL) was heated at 90° C. under microwave irradiation for 30 min, TLC (PE:EA=2:1) showed that the starting material was consumed. The reaction was repeated (50 mg of 26b was used) and the two reaction mixtures were combined and partitioned between EA/brine (20 mL/20 mL). The organic layer was collected, dried over Na$_2$SO$_4$, filtered and concentrated in vacuo. The residue was purified by chromatography (PE:EA=1:0 to 4:1) to give 26c (60 mg, 50%) as colorless oil. LC-MS (Agilent, P-2): R$_t$ 3.26 min; m/z calculated for C$_{30}$H$_{30}$N$_2$O$_3$ [M+H]$^+$ 467.2. found [M+H]$^+$ 467.3.

4. Procedure for the Preparation of 26

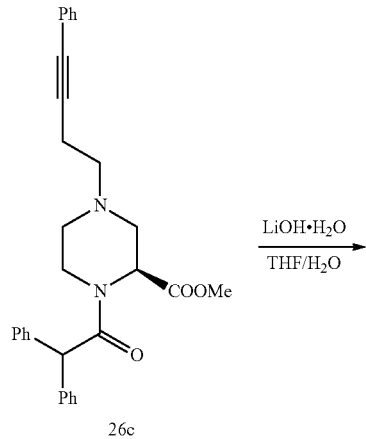

26c

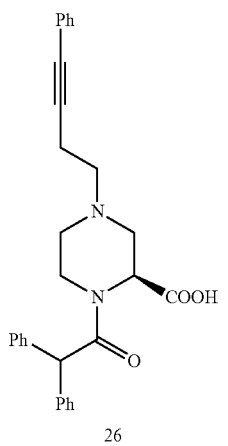

26

A mixture of 26c (60 mg, 0.12 mmol) and LiOH.H$_2$O (19 mg, 0.45 mmol) in THF/H$_2$O (3 mL/1 mL) was stirred at RT overnight, TLC (PE:EA=2:1) showed that the starting material was consumed. The mixture was concentrated in vacuo, the residue was dissolved in water (10 mL), acidified to pH 4~5 with a 4 M HCl aqueous solution and extracted with DCM (10 mL×2). The combined organic extracts were washed with brine (10 mL), dried over Na$_2$SO$_4$, filtered and concentrated in vacuo. The residue was purified by preparative HPLC to give 26 (55 mg, 94%) as a white solid. LC-MS (Agilent, P-2): R$_t$ 3.06 min; m/z calculated for C$_{29}$H$_{23}$N$_2$O$_3$ [M+H]$^+$ 453.2. found [M+H]$^+$ 453.2. HPLC (JULY-L) (214 and 254 nm): R$_t$ 9.31 min.

Example 14: Compound 27 (S)-1-(2,2-diphenylacetyl)-4-(4-(4-fluororophenyl)but-3-yn-1-yl)piperidine-2-carboxylic acid 1. Procedure for the Preparation of 27a

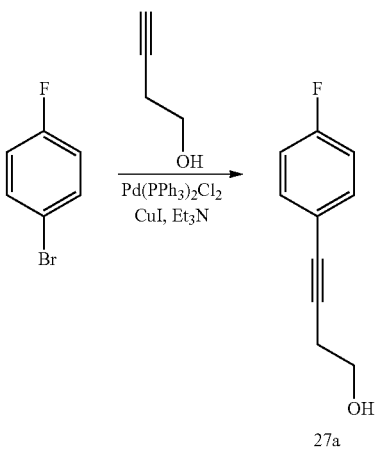

27a

To a solution of 1-bromo-4-fluorobenzene (2.00 g, 11.0 mmol) in THF (30 mL) was added but-3-yn-1 (0.88 g, 12 mmol), Et$_3$N (2.22 g, 22.0 mmol), CuI (104 mg, 0.55 mmol) and Pd(PPh$_3$)$_2$Cl$_2$ (700 mg, 1.1 mmol) and the mixture was heated at reflux under a N$_2$ atmosphere overnight, TLC (PE:EA=2:1) showed a new product formed. The mixture was cooled to RT, partitioned between EA/H$_2$O (30 mL/40 mL) and the organic layer was separated, washed with brine, dried over Na$_2$SO$_4$, filtered and concentrated in vacuo. The residue was purified by chromatography (PE:EA=1:0 to 3:1) to give 27a (200 mg, 9%) as a white solid.

2. Procedure for the Preparation of 27b

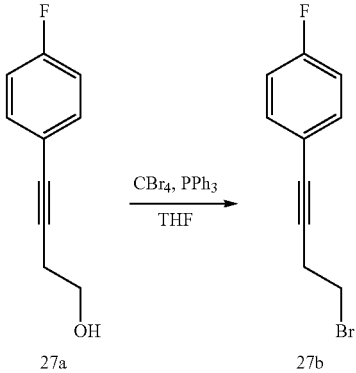 [SMILES: OCCC#Cc1ccc(F)cc1 ; Fc1ccc(C#CCCBr)cc1 ; "THF"]

27a        27b

To a solution 27a (200 mg, 1.22 mmol) and PPh$_3$ (319 mg, 1.22 mmol) in THF (10 mL) at 0° C. under a N$_2$ atmosphere was added CBr$_4$ (424 mg, 1.28 mmol) and the mixture was allowed to warm slowly to RT and stirred for 3 h. Another batch of PPh₃ (160 mg, 0.61 mmol) and CBr₄ (212 mg, 0.64 mmol) were added and stirring was continued at RT overnight, TLC (PE:EA=2:1) showed that most of the starting material was consumed. EA (2 mL) was added to the mixture followed by PE (5 mL) and the resulting precipitate was removed by filtration. The filtrate was concentrated in vacuo and the residue was purified by chromatography (100% PE) to give 27b (200 mg, 72%) as a colorless oil.

3. Procedure for the Preparation of 27c

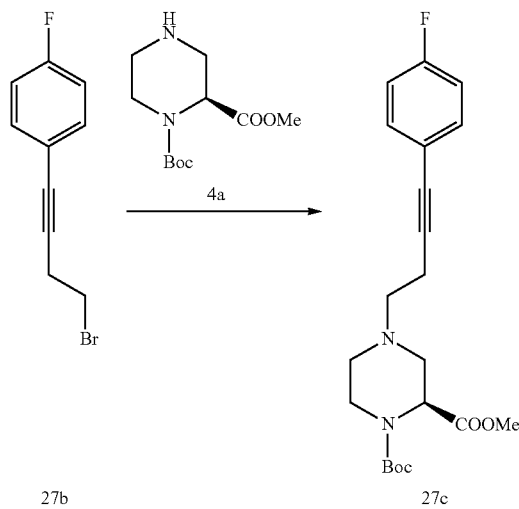

A mixture of 4a (215 mg, 0.88 mmol), 27b (200 mg, 0.88 mmol) and K₂CO₃ (146 mg, 1.06 mmol) in DMF (10 mL) was heated at 60° C. overnight, TLC (PE:EA=4:1) showed that most of the starting material was consumed. The mixture was poured into ice-water (50 mL), extracted with EA (15 mL×2) and the combined organic extracts were washed with brine, dried over Na₂SO₄, filtered and concentrated in vacuo. The residue was purified by chromatography (PE:EA=1:0 to 8:1) to give 27c (13 mg, 4%) as a colorless oil. LC-MS (Agilent, P-2): R$_t$ 3.11 min; m/z calculated for $C_{21}H_{27}FN_2O_4$[M+H]⁺ 391.2. Found [M+H]⁺ 391.2.

4. Procedure for the Preparation of 27d

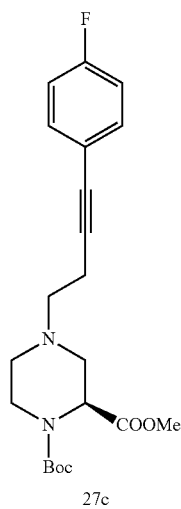

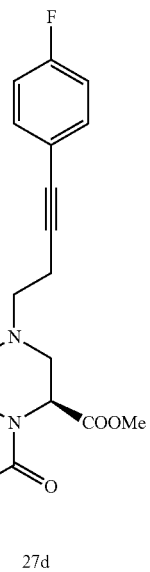

A mixture of 27c (13 mg, 0.033 mmol) in a 4 M HCl/MeOH solution (5 mL) was stirred at RT for 30 min, TLC (PE:EA=4:1) showed that the starting material was consumed. The mixture was concentrated in vacuo, DCM (10 mL) was added to the residue and then concentrated again in vacuo. The residue was dissolved in DCM (5 mL) and the solution was basified to pH 7 with Et₃N. More Et₃N (10 mg, 0.1 mmol) was added followed by diphenylacetyl chloride (8 mg, 0.033 mmol) and the mixture was stirred at RT overnight, TLC (PE:EA=2:1) showed a major new product formed. The mixture was washed with brine, dried over Na₂SO₄, filtered and concentrated in vacuo. The residue was purified by chromatography (PE:EA=6:1 to 4:1) to give 27d (11 mg, 66%) as a colorless oil. LC-MS (Agilent, P-2): R$_t$ 2.87 min; m/z calculated for $C_{30}H_{29}FN_2O_3$ [M+H]⁺ 485.2. found [M+H]⁺ 485.2.

5. Procedure for the Preparation of 27

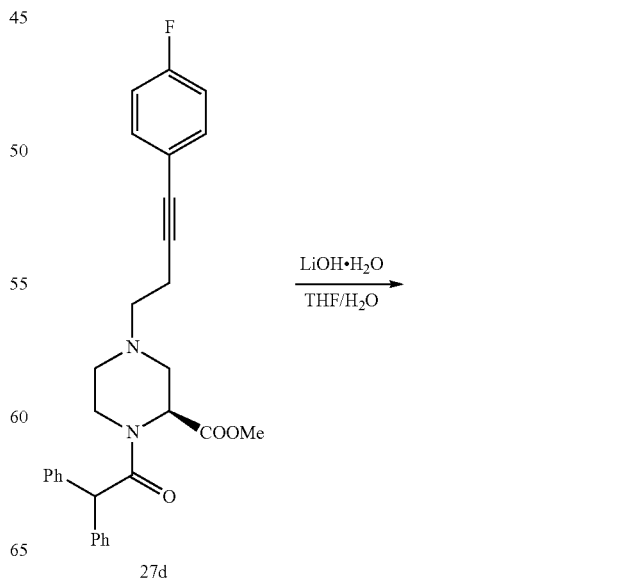

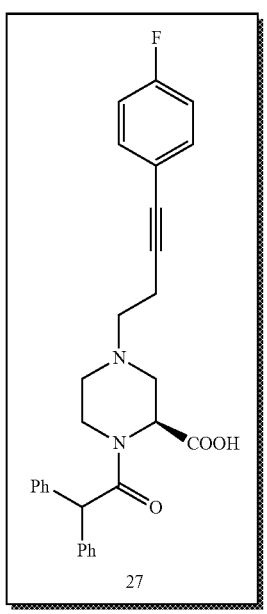

27

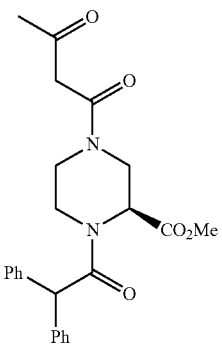

28b

To a solution of 28a (400 mg, 1.18 mmol) in toluene (10 mL) was added tert-butyl 3-oxobutanoate (187 mg, 1.18 mmol) and the mixture was heated at 100° C. overnight, TLC (DCM:MeOH=20:1) showed that the starting material was consumed. The mixture was cooled to RT and concentrated in vacuo to afford 28b (445 mg, 89%) as a colorless oil, which was used directly in the next step. LC-MS (Agilent, P-2): $R_t$ 2.592 min; m/z calculated for, $C_{24}H_{26}N_2O_5$ $[M+H]^+$ 423.2, $[M+Na]^+$ 445.2. found $[M+H]^+$ 423.2, $[M+Na]^+$ 445.2.

2. Procedure for the Preparation of 28c

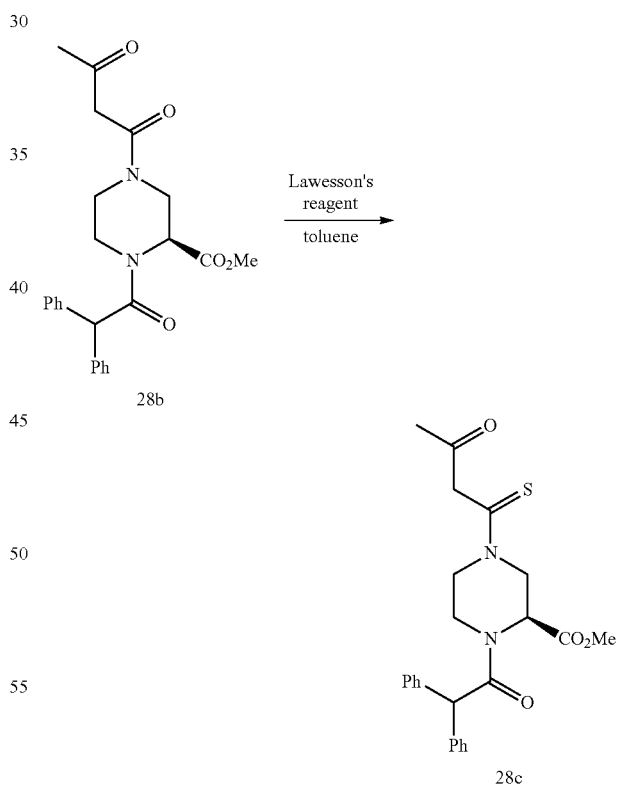

28c

A mixture of 27d (11 mg, 0.023 mmol) and LiOH.H$_2$O (3 mg, 0.068 mmol) in THF/H$_2$O (3 mL/1 mL) was stirred at RT overnight, then stirred at 27° C. for 5 h, TLC (PE:EA=2:1) showed that the starting material was consumed. The mixture was concentrated in vacuo to remove the THF and the residue was dissolved in water (10 mL), acidified to pH 4~5 with a 4 M aqueous HCl solution and extracted with DCM (10 mL×3). The combined organic extracts were washed with brine, dried over Na$_2$SO$_4$, filtered and concentrated in vacuo. The residue was purified by preparative HPLC to give 27 (7 mg, 66%) as a white solid. LC-MS (Agilent, P-2): $R_t$ 2.55 min; m/z calculated for $C_{29}H_{27}FN_2O_3$ $[M+H]^+$ 471.2. found $[M+H]^+$ 471.2. HPLC (JULY-L) (214 and 254 nm): $R_t$ 9.19 min.

Example 15: Compound 28 (S)-4-(1-benzyl-3-methyl-1H-pyrazolyl)-N—(N,N-dimethylsulfamoyl)-1-(2,2-diphenylacetyl)piperazine-2-carboxamide 1. Procedure for the Preparation of 28b.

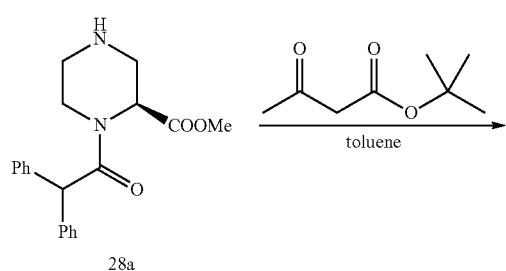

28a

To a stirred solution of 28b (445 mg, 1.05 mmol) in toluene (5 mL) was added Lawesson's reagent (213 mg, 0.527 mmol) and the mixture was heated at 75° C. overnight, TLC (PE:EA=1:2) showing that the starting material was consumed. The mixture was concentrated in vacuo and the residue was purified by chromatography (PE:EA=5:1 to 1:2) to give 28c (180 mg, 39%) as a pale yellow solid. LC-MS (Agilent, P-2): $R_t$ 2.522 min; m/z calculated for $C_{24}H_{26}N_2O_4S$ [M+Na]$^+$ 461.1. found [M+Na]$^+$ 461.1.

3. Procedure for the Preparation of 28d

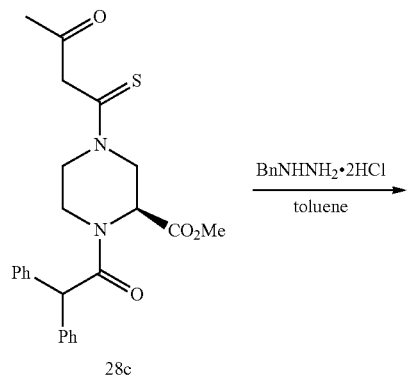
28c

To a solution of 28c (180 mg, 0.41 mmol) in toluene (10 mL) was added BnNHNH$_2$·2HCl (96 mg, 0.49 mmol) and the mixture was heated at 90° C. overnight, TLC (DCM:MeOH=50:1) showed that the starting material was consumed. The mixture was concentrated in vacuo and the residue was purified by chromatography (DCM:MeOH=1:0 to 50:1) to give 28d (105 mg, 50%) as a yellow solid. LC-MS (Agilent, P-2): $R_t$ 2.74 min; m/z calculated for $C_{31}H_{32}N_4O_3$ [M+H]$^+$ 509.3, [M+Na]$^+$ 531.3. found [M+H]$^+$ 509.2, [M+Na]$^+$ 531.2.

4. Procedure for the Preparation of 28e

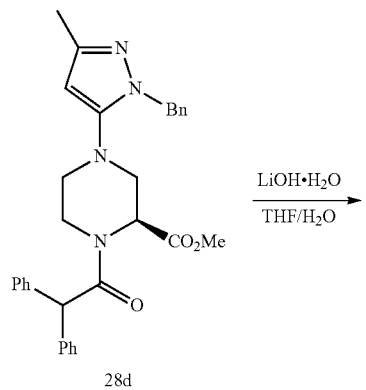
28d

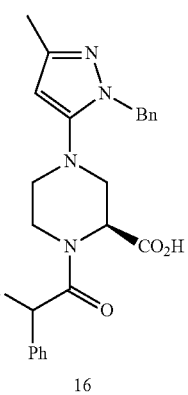
16

A mixture of 28d (105 mg, 0.21 mmol) and LiOH.H$_2$O (34 mg, 0.84 mmol) in THF/H$_2$O (3 mL/1 mL) was stirred at RT overnight, TLC (DCM:MeOH=20:1) showed that the starting material was consumed. The mixture was concentrated in vacuo to remove the THF, the residue was dissolved in water (30 mL), acidified to pH 4 with a 3 M aqueous HCl solution and extracted with DCM (20 mL×2). The combined organic extracts were washed with brine, dried over Na$_2$SO$_4$, filtered and concentrated in vacuo. The residue was purified by chromatography (DCM:MeOH=1:0 to 20:1) to give 16 (75 mg, 72%) as a yellow solid. LC-MS (Agilent, P-2): $R_t$ 2.80 min; m/z calculated for $C_{30}H_{30}N_4O_3$ [M+H]$^+$ 495.2. found [M+H]$^+$ 495.3.

5. Procedure for the Preparation of 28

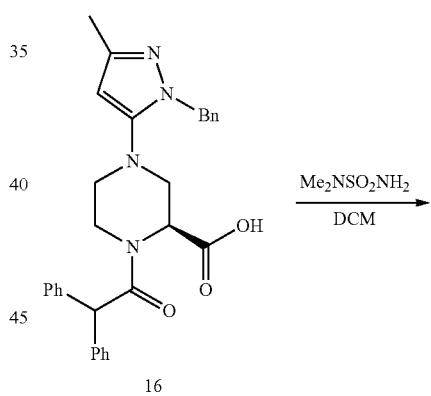
16

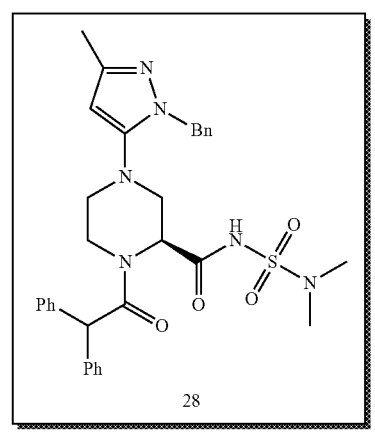
28

A mixture of 16 (70 mg, 0.14 mmol), N,N-dimethylsulfamide (17 mg, 0.17 mmol), DMAP (5 mg, 0.042 mmol) and DCC (35 mg, 0.17 mmol) in DCM (1 mL) was stirred at RT overnight, TLC (DCM:MeOH=10:1) showed that the starting material was consumed. The mixture was partitioned between DCM (20 mL) and brine (20 mL) and the organic layer was separated, dried over $Na_2SO_4$, filtered and concentrated in vacuo. The residue was purified by chromatography (DCM:MeOH=1:0 to 50:1) to give 28 (40 mg, 47%) as a yellow solid. LC-MS (Agilent, P-2): $R_t$ 2.77 min; m/z calculated for $C_{32}H_{36}N_6O_4S$ $[M+H]^+$ 601.3. found $[M+H]^+$ 601.3. HPLC (JULY-L) (214 and 254 nm): $R_t$ 9.41 min.

Biological Example 1

$AT_2$ Receptor Binding

Media and Solutions
1. Trypsin-EDTA (for preparation of 100 mL)
Trypsin 0.25 g
2% EDTA 2 mL
PBS 98 mL
Dissolve trypsin in 2% EDTA and PBS completely; sterilize the solution by passing through a 0.20 μM membrane filter; store at 4° C.
2. DMEM medium (for preparation of 1 L)
The powder was dissolved into 950 mL of distilled water with gentle stirring until the solution becomes clear.
Add $NaHCO_3$ 1.176 g for DMEM medium.
Adjust pH of medium to 0.2-0.3 below final working pH using 1 M NaOH or 1 M HCl. Add slowly with stirring.
Dilute to 1 liter with dd$H_2O$.
Sterilize the medium immediately by filtration.
Store at 4° C.
3. TE buffer
20 mM Tris-HCl, pH 7.4,
5 mM EDTA
4. Binding Assay Buffer
50 mM Hepes, pH 7.4
5 mM $MgCl_2$
1 mM $CaCl_2$
0.2% BSA
5. Wash Buffer
50 mM Hepes, pH 7.4

Procedures for HEK293/$AT_2$ Receptor Transient Cell Transfection
Cells were plated into 150 mm dish at 50% density for transient transfection. Cells were ready for transfection after overnight incubation (the confluence reaches around 80%).
75 μL Lipofectamine™2000 diluted in 6.25 mL OptiMEM I Reduced Serum Medium, was mixed gently, and incubated at room temperature for 5 minutes.
50 μg expression plasmid DNA diluted in 6.25 mL OptiMEM I Reduced Serum Medium without serum was mixed gently.
After the 5 minute incubation, the diluted DNA was combined with the diluted Lipofectamine™2000 (total volume is 12.5 mL). The mixture was mixed gently and incubated for 30 minutes at room temperature to allow the DNA-Lipofectamine™2000 complexes to form.
The 12.5 mL DNA-Lipofectamine™2000 complexes were added into the 150 mm dish and mixed gently by rocking the dish back and forth.
The cells were incubated at 37° C. with 5% $CO_2$ for 48 hours.
Cells were collected and stored frozen at −80° C.

Procedures for HEK293/$AT_2$ Receptor Cell Membrane Preparation
Frozen HEK293/$AT_2$ receptor (transient transfected) cells were homogenized in ice cold TE buffer for 10 s.
The homogenate was centrifuged at 25,000 g for 30 minutes.
The pellet was resuspended in ice cold tissue buffer.
Protein concentrations were determined using Bradford assay method with BSA as standard.
The membrane protein was frozen under −80° C.

Compound Preparation
Solutions of all compounds were prepared by microplate liquid handling equipment such as Janus or Precision 2000. Compounds, dissolved in DMSO were stored in a Freezer. Compounds were prepared from 30 mM in 100% DMSO.
Step 1: Dose plate preparation (96 well plate)
Add the 3 μL [30 mM] compound stock to column 1 on the plate.
Add 15 μL of 100% DMSO to column 1.
Add 10.81 μL of 100% DMSO to column 2-12.
Transfer 5 μL from column 1 into column 2 (half log dilution).
Transfer 5 μL from column 2 into column 3 (half log dilution).
Transfer 5 μL from column 3 into column 4 (half log dilution).
Transfer 5 μL from column 4 into column 5 (half log dilution).
Transfer 5 μL from column 5 into column 6 (half log dilution).
Transfer 5 μL from column 6 into column 7 (half log dilution).
Transfer 5 μL from column 7 into column 8 (half log dilution).
Transfer 5 μL from column 8 into column 9 (half log dilution).
Transfer 5 μL from column 9 into column 10 (half log dilution)
Transfer 5 μL from column 10 into column 11 (half log dilution)
Transfer 5 μL from column 11 into column 12 (half log dilution).
All the compounds were diluted using Precision 2000 microplate liquid handling equipment. The top concentration of compound was 5 mM with 100% DMSO.
Step 2: Working plate preparation (96 well plate)
Compounds were diluted 50-fold with buffer.
49 μL buffer was added to the well of 96 well plate.
1 μL compound solution from dose plate was transferred to the corresponding well of working plate.
The top concentration of compound was 100 μM with 2% DMSO.
Step 3: Assay plate preparation (96 well plate)
15 μL of compound solution was transferred from each well of working plate to the well of assay plate by Janus. Each compound was assayed in duplicate in each plate and there were 4 compounds per plate.
Procedures for $AT_2$ Receptor Binding Assay
120 μL membrane (5 mg protein/well) was incubated with 15 μL of [$^{125}$I]-CGP42112A and 15 μL of compound at RT for 1.5 hrs.
The binding reaction was stopped by rapid filtration through Unifilter GF/C plates (presoaked in 0.3% (v:v) BSA).
Plate was washed three times with ice cold wash buffer.
The filtration plates were dried at 37° C. overnight.
50 μL of scintillation cocktail was added to each well.

Radioactivity was determined using MicroBetaTriltuunicroplate scintillation counter.

Data Analysis

Data was analyzed through 4 parameter logic using Prism 5.0 software.

The results are shown in the following Table:

| Compound | IC$_{50}$ (nM) |
| --- | --- |
| 4 | 408 |
| 5 | 383.2 |
| 6 | 3045 |
| 7 | 155 |
| 8 | 1267 |
| 9 | 4105 |
| 10 | 517.1 |
| 16 | 40.26 |
| 23 | 93.85 |
| 24 | 4161 |
| 25 | 3923 |
| 26 | 1319 |

Biological Example 2

AT$_1$ Receptor Binding

Evaluation of the affinity of the test compounds for the human angiotensin-II AT$_1$ receptor in transfected HEK-293 cells was determined in a radioligand assay (Le, et al., *Eur. J. Pharmacol.*, 2005, 513:35).

Cell membrane homogenates (8 μg protein) were incubated for 120 min at 37° C. with 0.005 nM [125][Sar1-Ile8] angiotensin-II in the absence or presence of the test compound in a buffer containing 50 mM Tris-HCl (pH 7.4), 5 mM MgCl$_2$, 1 mM EDTA and 0.1% BSA. Nonspecific binding was determined in the presence of 10 mM angiotensin-II.

Following incubation, the samples were filtered rapidly under vacuum through glass fibre filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results were expressed as a percent inhibition of the control radioligand specific binding.

The standard reference compound was saralasin, which was tested in each experiment at several concentrations to obtain a competition curve from which its IC$_{50}$ was calculated.

The assay was performed in a volume of 200 μL in a 96 well plate. Test compounds used were compounds 16 and 23.

Neither compound had sufficient binding activity for the AT$_1$ receptor to allow an IC$_{50}$ to be determined. The maximum concentration of test compound used was 10 μM.

REFERENCES

Chakrabarty et al., 2008, Estrogen elicits dorsal root ganglion axon sprouting via a rennin-angiotensin system. *Endocrinology*, 149(7):3452-3460.

Clere et al., 2010, Deficiency or blockade of angiotensin II type 2 receptor delays tumorigenesis by inhibiting malignant cell proliferation and angiogenesis. *Int. J. Cancer*, 127: 2279-2291.

Izu et al., 2009, Angiotensin II Type 2 receptor blockade increases bone mass. *J. Biol. Chem.*, 284(8):4857-4864.

Steckelings et al., 2005, The AT$_2$ receptor—A matter of love and hate. *Peptides*, 26:1401-1409.

Wallinder et al., 2008, Selective angiotensin II AT$_2$ receptor agonists: Benzamide structure-activity relationships. *Bioorganic & Medicinal Chemistry*, 16:6841-6849.

Wan et al., 2004, Design, Synthesis and biological evaluation of the first selective nonpeptide AT$_2$ receptor agonist. *J. Med Chem.*, 47:5995-6008.

Wexler et al., 1996, Nonpeptide angiotensin II receptor antagonists: The next generation in antihypertensive therapy. *J. Med. Chem.;* 39 (3):325-656.

What is claimed:

1. A compound of formula (I):

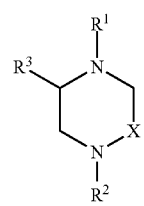

(I)

wherein

X is —CHR$^4$—;

R$^1$ is —C(=O)CH(phenyl)(phenyl);

R$^2$ is phenyl, benzyl, —CH$_2$CH$_2$phenyl, —CH$_2$CH=CH-phenyl, —CH$_2$C≡C-phenyl, —CH$_2$C≡C-4-fluorophenyl, —CH$_2$CH$_2$C≡C-phenyl, —CH$_2$CH$_2$CH$_2$phenyl, -(3-methyl-1-phenyl-1H-pyrazol-5yl); -(1,5-diphenyl-1H-pyrazol-3-yl); -(1-benzyl-3-methyl-1H-pyrazol-5-yl); or -(1-benzyl-3-(trifluoromethyl)-1H-pyrazolyl-5-yl);

R$^3$ is —CO$_2$H, —CH$_2$CO$_2$H, —C(=O)NH$_2$, —CN, —C(=O)C(=O)OH, —C(=O)NHSO$_2$C$_{1-6}$alkyl, —C(=O)NHSO$_2$phenyl, —C(O)NHSO$_2$N(CH$_3$)$_2$, —C(=O)NHSO$_2$CF$_3$, —SO$_3$H or —PO$_3$H$_2$;

R$^4$ is hydrogen;

R$^7$ is hydrogen, —C$_{1-6}$alkyl, aryl or —C$_{1-6}$alkylenearyl; wherein each aryl is optionally substituted with one or more substituents independently selected from C$_{1-6}$alkyl, halogen, phenyl, benzyl and CF$_3$;

or a pharmaceutically acceptable salt thereof.

2. A compound according to claim 1 wherein R$^3$ is —CO$_2$H; or a pharmaceutically acceptable salt thereof.

3. A pharmaceutical composition comprising a compound of formula (I) according to claim 1 or a pharmaceutically acceptable salt thereof and a pharmaceutically acceptable carrier.

4. A compound according to claim 1 selected from the group consisting of:

(S)-1-(2,2-diphenylacetyl)-4-phenylpiperazine-2-carboxylic acid;

(S)-4-benzyl-1-(2,2-diphenylacetyl)piperazine-2-carboxylic acid;

(S)-4-(1,5-diphenyl-1H-pyrazol-3-yl)-1-(2,2-diphenylacetyl)-piperazine-2-carboxylic acid;

(S)-1-(2,2-diphenylacetyl)-4-(3-methyl-1-phenyl-1H-pyrazol-5-yl)piperazine-2-carboxylic acid;

(S)-1-(2,2-diphenylacetyl)-4-phenethylpiperazine-2-carboxylic acid;

(S)-4-cinnamyl-1-(2,2-diphenylacetyl)piperazine-2-carboxylic acid;

(S)-1-(2,2-diphenylacetyl)-4-(3-phenylpropyl)piperazine-2-carboxylic acid;
(S)-4-(1-benzyl-3-methyl-1H-pyrazol-5-yl)-1-(2,2-diphenylacetyl)piperazine-2-carboxylic acid;
(S)-4-(1-benzyl-3-(-trifluoromethyl)-1H-pyrazol-5-yl)-1-(2,2-diphenylacetyl) piperazine-2-carboxylic acid;
(S)-1-(2,2-diphenylacetyl)-4-(3-phenylprop-2-yn-1-yl) piperazine-2-carboxylic acid;
(S)-1-(2,2-diphenylacetyl)-4-(4-phenylbut-3-yn-1-yl)piperazine-2-carboxylic acid; and

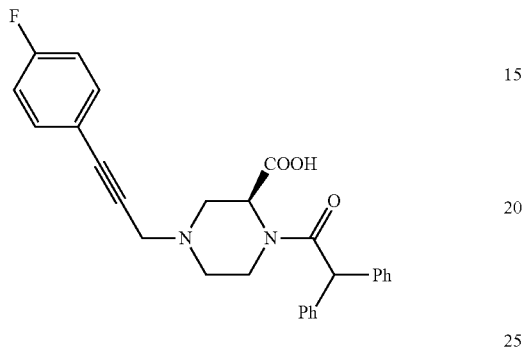

or pharmaceutically acceptable salts thereof.

5. A pharmaceutical composition comprising a compound according to claim 4 or a pharmaceutically acceptable salt thereof and a pharmaceutically acceptable carrier.

6. A pharmaceutical composition comprising a compound according to claim 2 or a pharmaceutically acceptable salt thereof and a pharmaceutically acceptable carrier.

* * * * *